(12) United States Patent
Fallon et al.

(10) Patent No.: US 10,716,835 B2
(45) Date of Patent: *Jul. 21, 2020

(54) METHODS AND COMPOSITIONS FOR THE PREVENTION AND TREATMENT OF INFLUENZA

(71) Applicant: Curemark, LLC, Rye Brook, NY (US)

(72) Inventors: Joan M. Fallon, White Plains, NY (US); Matthew Heil, Sherman, CT (US); James Fallon, Armonk, NY (US); James Szigethy, Montgomery, NY (US)

(73) Assignee: CUREMARK, LLC, Rye Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/265,620

(22) Filed: Sep. 14, 2016

(65) Prior Publication Data

US 2017/0202934 A1  Jul. 20, 2017

Related U.S. Application Data

(63) Continuation of application No. 13/502,989, filed as application No. PCT/US2010/053484 on Oct. 21, 2010, now Pat. No. 9,511,125.

(60) Provisional application No. 61/253,805, filed on Oct. 21, 2009.

(51) Int. Cl.
| | |
|---|---|
| *A61K 38/54* | (2006.01) |
| *A61K 38/47* | (2006.01) |
| *A61K 38/48* | (2006.01) |
| *A61K 38/46* | (2006.01) |
| *A61K 9/00* | (2006.01) |
| *A61K 39/145* | (2006.01) |
| *A61K 39/00* | (2006.01) |
| *C12N 7/00* | (2006.01) |

(52) U.S. Cl.
CPC ............ *A61K 38/54* (2013.01); *A61K 9/0014* (2013.01); *A61K 9/0053* (2013.01); *A61K 38/465* (2013.01); *A61K 38/47* (2013.01); *A61K 38/4826* (2013.01); *A61K 38/4873* (2013.01); *A61K 39/145* (2013.01); *C12N 7/00* (2013.01); *A61K 2039/5252* (2013.01); *A61K 2039/5254* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 3,002,883 A | 10/1961 | Butt et al. | |
| 3,223,594 A | 12/1965 | Hoek | |
| 3,322,626 A | 5/1967 | D'Argento | |
| 3,357,894 A | 12/1967 | Uriel et al. | |
| 3,515,642 A | 6/1970 | Hiroyuki et al. | |
| 3,574,819 A | 4/1971 | Franz et al. | |
| 3,860,708 A | 1/1975 | Prout | |
| 3,940,478 A | 2/1976 | Kurtz | |
| 4,079,125 A | 3/1978 | Sipos | |
| 4,145,410 A | 3/1979 | Sears | |
| 4,241,046 A | 12/1980 | Papahadjopoulos et al. | |
| 4,280,971 A | 7/1981 | Wischniewski et al. | |
| 4,447,412 A | 5/1984 | Bilton | |
| 4,456,544 A | 6/1984 | Lupova et al. | |
| 4,500,515 A | 2/1985 | Libby | |
| 4,623,624 A | 11/1986 | Schultze | |
| 4,826,679 A | 5/1989 | Roy | |
| 5,023,108 A | 6/1991 | Bagaria et al. | |
| 5,190,775 A | 3/1993 | Klose | |
| 5,227,166 A | 7/1993 | Ueda et al. | |
| 5,250,418 A | 10/1993 | Moeller et al. | |
| 5,324,514 A | 6/1994 | Sipos | |
| 5,378,462 A | 1/1995 | Boedecker et al. | |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS

Cichoke, A.J. Influenza. In: The Complete Book of Enzyme Therapy. Copyright 1999 Anthony J. Cichoke. Publisher: Avery, a member of Penguin Putnam, Inc. Ed.: Dara Stewart, pp. 50, 273, 274, 454, 455.*

Roxas, M. et al. 2007. Colds and Influenza: A review of diagnosis and conventional, botanical, and nutritional considerations. Alternative Medicine Review 12(1): 25-48.*

Cox, R.J. et al. 2004. Influenza virus: Immunity and vaccination strategies. Comparison of the immune response to inactivated and live, attenuated influenza vaccines. Scandinavian Journal of Immunology 59: 1-15; specif. pg. 1.*

(Continued)

*Primary Examiner* — Thomas J. Visone
*Assistant Examiner* — Sharon M. Papciak
(74) *Attorney, Agent, or Firm* — Wilson Sonsini Goodrich & Rosati

(57) ABSTRACT

This disclosure relates to the prevention and treatment of Influenza, and more particularly Influenza A Virus Subtype H1N1, with the use of a pharmaceutical composition comprising one or more digestive enzymes, such as pancreatic enzymes and porcine pancreatic enzymes. The disclosure further relates to the use of an individual's fecal chymotrypsin level as an indicator, e.g., biomarker of whether an individual may be more susceptible to Influenza, e.g., Influenza A Subtype H1N1, and/or whether an individual will benefit from administration of the described pharmaceutical compositions. Use of the compositions as sanitizers, antiseptics, disinfectants, and detergents, e.g., to reduce or eradicate influenza virus present on living or inanimate surfaces is also contemplated.

27 Claims, No Drawings

(56) References Cited

U.S. PATENT DOCUMENTS

| | | |
|---|---|---|
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,607,863 A | 3/1997 | Chandler |
| 5,648,335 A | 7/1997 | Lewis et al. |
| 5,674,532 A | 10/1997 | Atzl et al. |
| 5,686,311 A | 11/1997 | Shaw |
| 5,750,104 A | 5/1998 | Sipos |
| 5,753,223 A | 5/1998 | Shibahara et al. |
| 5,776,917 A | 7/1998 | Blank et al. |
| 5,858,758 A | 1/1999 | Hillman et al. |
| 5,952,178 A | 9/1999 | Lapidus et al. |
| 5,958,875 A | 9/1999 | Longo et al. |
| 5,977,175 A | 11/1999 | Lin |
| 5,985,891 A | 11/1999 | Rowe |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,096,338 A | 8/2000 | Lacy et al. |
| 6,100,080 A | 8/2000 | Johansen |
| 6,149,585 A | 11/2000 | Gray |
| 6,153,236 A | 11/2000 | Wu et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,238,727 B1 | 5/2001 | Takemoto et al. |
| 6,251,478 B1 | 6/2001 | Pacifico et al. |
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,632,429 B1 | 10/2003 | Fallon |
| 6,660,831 B2 | 12/2003 | Fallon |
| 6,699,885 B2 | 3/2004 | Phillips |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,890,561 B1 | 5/2005 | Blatt et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,163,278 B2 | 4/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,486,390 B2 | 7/2013 | Fallon |
| 8,580,522 B2 | 11/2013 | Fallon |
| 8,613,918 B2 | 12/2013 | Fallon |
| 8,658,163 B2 | 2/2014 | Fallon |
| 8,673,877 B2 | 3/2014 | Fallon et al. |
| 8,778,335 B2 | 7/2014 | Fallon |
| 8,815,233 B2 | 8/2014 | Fallon |
| 8,921,054 B2 | 12/2014 | Fallon |
| 8,980,252 B2 | 3/2015 | Fallon et al. |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 9,233,146 B2 | 1/2016 | Fallon |
| 9,320,780 B2 | 4/2016 | Fallon |
| 9,345,721 B2 | 5/2016 | Fallon |
| 9,377,459 B2 | 6/2016 | Fallon |
| 9,492,515 B2 | 11/2016 | Fallon et al. |
| 9,624,525 B2 | 4/2017 | Fallon |
| 9,624,526 B2 | 4/2017 | Fallon |
| 10,098,844 B2 | 10/2018 | Fallon |
| 10,350,278 B2 | 7/2019 | Fallon et al. |
| 2001/0006644 A1 | 7/2001 | Bova et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0026892 A1 | 2/2005 | Bodor |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |

(56) References Cited

U.S. PATENT DOCUMENTS

| | | |
|---|---|---|
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0253045 A1 | 11/2006 | Coifman |
| 2006/0258599 A1 | 11/2006 | Childers |
| 2006/0259995 A1 | 11/2006 | Cayouette et al. |
| 2006/0294108 A1 | 12/2006 | Adelson et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon et al. |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0177578 A1 | 7/2008 | Zakim |
| 2008/0187525 A1 | 8/2008 | Porubcan |
| 2008/0199448 A1 | 8/2008 | Ross et al. |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0004285 A1 | 1/2009 | Yu et al. |
| 2009/0110674 A1 | 4/2009 | Loizou |
| 2009/0117180 A1 | 5/2009 | Ortenzi et al. |
| 2009/0171696 A1 | 7/2009 | Allard et al. |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0065628 A1 | 3/2011 | Johnson et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0027848 A1 | 2/2012 | Fallon et al. |
| 2012/0070504 A1 | 3/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0258149 A1 | 10/2012 | Fallon et al. |
| 2013/0059001 A1 | 3/2013 | Fallon |
| 2013/0095152 A1 | 4/2013 | Fallon |
| 2013/0113129 A1 | 5/2013 | Fallon et al. |
| 2013/0202581 A1 | 8/2013 | Fallon et al. |
| 2013/0224172 A1 | 8/2013 | Fallon et al. |
| 2014/0147500 A1 | 5/2014 | Fallon et al. |
| 2014/0348881 A1 | 11/2014 | Fallon |
| 2015/0023944 A1 | 1/2015 | Fallon |
| 2015/0147308 A1 | 5/2015 | Fallon et al. |
| 2015/0150955 A1 | 6/2015 | Fallon et al. |
| 2015/0174219 A1 | 6/2015 | Fallon |
| 2015/0174220 A1 | 6/2015 | Fallon |
| 2015/0182607 A1 | 7/2015 | Jolly et al. |
| 2015/0246104 A1 | 9/2015 | Fallon et al. |
| 2015/0246105 A1 | 9/2015 | Fallon et al. |
| 2015/0273030 A1 | 10/2015 | Fallon |
| 2015/0335589 A1 | 11/2015 | Fallon et al. |
| 2016/0045576 A1 | 2/2016 | Fallon et al. |
| 2016/0206708 A1 | 7/2016 | Fallon et al. |
| 2016/0213697 A1 | 7/2016 | Fallon |
| 2016/0266113 A1 | 9/2016 | Fallon |
| 2016/0287683 A1 | 10/2016 | Fallon |
| 2018/0161409 A1 | 6/2018 | Fallon |
| 2018/0243282 A1 | 8/2018 | Fallon |
| 2018/0296650 A1 | 10/2018 | Fallon |
| 2019/0175704 A1 | 6/2019 | Fallon |
| 2019/0183990 A1 | 6/2019 | Fallon et al. |
| 2019/0201507 A1 | 7/2019 | Fallon |
| 2019/0209667 A1 | 7/2019 | Fallon |
| 2019/0275066 A1 | 9/2019 | Fallon et al. |
| 2019/0275128 A1 | 9/2019 | Fallon et al. |
| 2020/0101145 A1 | 4/2020 | Fallon et al. |

FOREIGN PATENT DOCUMENTS

| | | | |
|---|---|---|---|
| CA | 2667976 A1 | 5/2008 | |
| CN | 1031562 | 3/1989 | |
| CN | 1329923 A | 1/2002 | |
| CN | 1552836 A | 12/2004 | |
| CN | 1791430 A | 6/2006 | |
| CN | 101039667 A | 9/2007 | |
| CN | 101208092 A | 6/2008 | |
| CN | 102984941 A | 3/2013 | |
| DE | 3738599 A1 | 5/1989 | |
| DE | 4332985 A1 | 3/1995 | |
| EP | 0425214 A2 | 5/1991 | |
| EP | 0436110 A1 | 7/1991 | |
| EP | 0451484 A1 | 10/1991 | |
| EP | 0564739 A2 | 10/1993 | |
| EP | 0564739 A3 | 4/1995 | |
| EP | 1162995 B1 | 6/2003 | |
| EP | 1413202 A1 | 4/2004 | |
| EP | 1335706 B1 | 4/2005 | |
| EP | 1019072 B1 | 5/2005 | |
| EP | 1604677 A1 | 12/2005 | |
| EP | 1931317 B1 | 12/2008 | |
| EP | 2258837 A1 | 12/2010 | |
| EP | 2318035 A1 | 5/2011 | |
| GB | 669782 A | 4/1952 | |
| GB | 2347742 A | 9/2000 | |
| GB | 2480772 A | 11/2011 | |
| JP | S62230714 A | 10/1987 | |
| JP | H04364119 A | 12/1992 | |
| JP | 2004500591 A | 1/2004 | |
| JP | 2005515223 A | 5/2005 | |
| JP | 2006512091 A | 4/2006 | |
| JP | 2007523664 A | 8/2007 | |
| JP | 2008283895 A | 11/2008 | |
| JP | 2013517251 A | 5/2013 | |
| KR | 20050084485 A | 8/2005 | |
| RU | 2356244 C1 | 5/2009 | |
| TW | 310277 B | 7/1997 | |
| WO | WO-8402846 A1 | 8/1984 | |
| WO | WO-8908694 A1 | 9/1989 | |
| WO | WO-9002562 A1 * | 3/1990 | ......... A61K 38/4873 |
| WO | WO-9419005 A1 | 9/1994 | |
| WO | WO-9522344 A1 | 8/1995 | |
| WO | WO-9732480 A1 | 9/1997 | |
| WO | WO-9822499 A2 | 5/1998 | |

(56) References Cited

FOREIGN PATENT DOCUMENTS

| | | |
|---|---|---|
| WO | WO-9826807 | 6/1998 |
| WO | WO-9822499 A3 | 7/1998 |
| WO | WO-9832336 A2 | 7/1998 |
| WO | WO-9852593 A1 | 11/1998 |
| WO | WO-9964059 A2 | 12/1999 |
| WO | WO-0009142 A1 | 2/2000 |
| WO | WO-9964059 A3 | 3/2000 |
| WO | WO-0021504 A1 | 4/2000 |
| WO | WO-0127612 A2 | 4/2001 |
| WO | WO-0143764 A2 | 6/2001 |
| WO | WO-0145835 A1 | 6/2001 |
| WO | WO-0127612 A3 | 10/2001 |
| WO | WO-0143764 A3 | 11/2001 |
| WO | WO-0214537 A2 | 2/2002 |
| WO | WO-0219828 A1 | 3/2002 |
| WO | WO-0214537 A3 | 5/2002 |
| WO | WO-02051352 A2 | 7/2002 |
| WO | WO-02051436 A2 | 7/2002 |
| WO | WO-03051345 A2 | 6/2003 |
| WO | WO-03059088 A1 | 7/2003 |
| WO | WO-2004060074 A1 | 7/2004 |
| WO | WO-2004093883 A2 | 11/2004 |
| WO | WO-2005115445 A1 | 12/2005 |
| WO | WO-2006031554 A2 | 3/2006 |
| WO | WO-2006044529 A1 | 4/2006 |
| WO | WO-2006031554 A3 | 9/2006 |
| WO | WO-2007002572 A2 | 1/2007 |
| WO | WO-2007074454 A2 | 7/2007 |
| WO | WO-2007147714 A1 | 12/2007 |
| WO | WO-2008021987 A2 | 2/2008 |
| WO | WO-2008102264 A2 | 8/2008 |
| WO | WO-2009114757 A2 | 9/2009 |
| WO | WO-2009155689 A1 | 12/2009 |
| WO | WO-2010002972 A1 | 1/2010 |
| WO | WO-2010025126 A1 | 3/2010 |
| WO | WO-2010080830 A1 | 7/2010 |
| WO | WO-2010080835 A1 | 7/2010 |
| WO | WO-2010120781 A1 | 10/2010 |
| WO | WO-2011000924 A1 | 1/2011 |
| WO | WO-2011114225 A1 | 9/2011 |
| WO | WO-2012145651 A2 | 10/2012 |
| WO | WO-2013103746 A1 | 7/2013 |
| WO | WO-2013116732 A1 | 8/2013 |
| WO | WO-2013181447 A1 | 12/2013 |

OTHER PUBLICATIONS

Cichoke, A..J. Influenza. In: The Complete Book of Enzyme Therapy. Copyright 1999. Anthony J. Cichoke. Avery, a member of Penguin Putnam, Inc., publisher. Ed.: Dara Stewart, pp. 37, 40-45. specif. pp. 40, 43.*

Dudzinska, N.M. Dissertation. Development of lipid-based enteric coatings. Oct. 18, 1988. Martin Luther University, Halle-Wittenberg. pp. 1-125. specif. pp. 1, 36.*

Carroccio, A. et al. 1997. Role of pancreatic impairment in growth recovery during gluten-free diet in childhood celiac disease. Gastroenterology 112: 1839-1844. specif. pp. 1839, 1840, 1842, 1843.*

Klopfleisch, R. et al. 2007. Encephalitis in a stone marten (Martes foina) after natural infection with highly pathogenic avian influenza virus subtype H5N1. Journal of Comparative Pathology 137: 155-159. specif. pp. 155, 156.*

Durie, P. et al. 1998. Uses and abuses of enzyme therapy in cystic fibrosis. Journal of the Royal Society of Medicine. 91:(Suppl. 34): 2-13. specif. pp. 2, 7, 8, 10.*

DeFelice, K. Viruses Part 2—results of two informal studies, Chapter 14. In: Enzymes: Go With Your Gut—more practical guidelines for digestive enzymes.Copyright 2006. Karen DeFelice. Published by ThunderSnow Interactive. pp. 195-218. specif. pp. 201, 202, 204, 205, 206, 207.*

Capua, I. et al. 2013. Influenza A viruses grow in human pancreatic cells and cause pancreatitis and diabetes in an animal model. Journal of Virology 87(1): 597-610. specif. pp. 597, 601.*

Co-pending U.S. Appl. No. 15/593,121, filed May 11, 2017.
Co-pending U.S. Appl. No. 15/593,124, filed May 11, 2017.
Co-pending U.S. Appl. No. 15/593,129, filed May 11, 2017.
U.S. Appl. No. 12/054,343 Final Office Action dated May 10, 2017.
U.S. Appl. No. 13/733,873 Non-Final Office Action dated May 25, 2017.
U.S. Appl. No. 13/836,135 Final Office Action dated May 15, 2017.
U.S. Appl. No. 14/693,711 Notice of Allowability dated May 26, 2017.
U.S. Appl. No. 14/921,896 Office Action dated Apr. 26, 2017.
Button, KS et al. Power failure: why small sample size undermines the reliability of neuroscience. Nat. Rev. Neurosci. 14:365376 (2013).
Clark et al., The effect of ranitidine versus proton pump inhibitors on gastric secretions: a meta-analysis of randomized control trials, Anaesthesia, 2009, 64, pages 652-657.
Co-pending U.S. Appl. No. 15/440,942, filed Feb. 23, 2017.
Riedel, L et al. Limitations of faecal chymotrypsin as a screening test for chronic pancreatitis. Gut, 32:321-324 (1991).
U.S. Appl. No. 13/002,136 Non-Final Office Action dated Feb. 27, 2017.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/503,844 Office Action dated Mar. 27, 2017.
U.S. Appl. No. 13/757,412 Office Action dated Feb. 10, 2017.
U.S. Appl. No. 14/296,091 Final Office Action dated Jan. 3, 2017.
U.S. Appl. No. 14/639,425 Notice of Allowance dated Mar. 10, 2017.
U.S. Appl. No. 14/693,711 Final Office Action dated Dec. 15, 2016.
U.S. Appl. No. 14/713,178 Advisory Office Action dated Jan. 19, 2017.
U.S. Appl. No. 14/713,221 Non-Final Office Action dated Dec. 30, 2016.
U.S. Appl. No. 14/713,242 Office Action dated Dec. 7, 2016.
U.S. Appl. No. 14/713,178 Notice of Allowance dated Apr. 12, 2017.
Anonymous: Emulsifiers forthe preparation of active dry yeast, Research Disclosure, Mason Publications, Hampshire, GB, 236(6), Dec. 1983 (attached).
Cichoke, AJ The Complete Book of Enzyme Therapy, Penguin (1999) pp. 206-208 and 38.
Co-pending U.S. Appl. No. 15/265,415, filed Sep. 14, 2016.
Co-pending U.S. Appl. No. 15/354,940, filed Nov. 17, 2016.
CREON—FDA Prescribing information side effects and uses. Revised Apr. 2015.
Life Plus Somazyne accessed Jun. 10, 2016, Online at www.lifeplus.com/media/pdf/piSheets/US/ 6141-PI_EN.pdf.
Michael's Naturopathic Programs, Digestive Enzymes, Product #011161, Accessed on Jun. 10, 2016, online at: www.michaelshealth.com/retail/digestive-enzymes-659.html.
Reeves, G. et al. Pharmacological Management of Attention-deficit hyperactivity disorder, Expert Opinion on Pharmacotherapy, 5:6; 1313-1320. (Feb. 25, 2005).
ULTRESA—FDA Prescribing Information Side Effects and Uses. Revised Sep. 2014.
U.S. Appl. No. 11/533,818 Final Office Action dated Jun. 7, 2016.
U.S. Appl. No. 12/054,343 Office Action dated Aug. 19, 2016.
U.S. Appl. No. 12/535,676 Office Action dated Sep. 13, 2016.
U.S. Appl. No. 12/786,739 Office Action dated Sep. 20, 2016.
U.S. Appl. No. 13/002,136 Final Office Action dated Jun. 24, 2016.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/503,844 Office Action dated Aug. 25, 2016.
U.S. Appl. No. 13/757,412 Final Office Action dated Jun. 30, 2016.
U.S. Appl. No. 13/836,135 Office Action dated Jul. 22, 2016.
U.S. Appl. No. 14/612,580 Office Action dated Sep. 21, 2016.
U.S. Appl. No. 14/612,604 Notice of Allowance dated Jul. 20, 2016.
U.S. Appl. No. 14/639,425 Office Action dated Jul. 14, 2016.
U.S. Appl. No. 14/713,178 Final Office Action dated Oct. 14, 2016.

(56) References Cited

OTHER PUBLICATIONS

U.S. Appl. No. 14/713,221 Final Office Action dated Jun. 16, 2016.
VIOKACE—FDA Prescribing Information, Side Effects and Uses. Revised Mar. 2012.
ZENPEP—FDA Prescribing Information, Side Effects and Uses. Revised Sep. 2014.
ABCnews. Changing Face of Autism: Numbers Rise as More Behaviors Included. ABCnews. Nov. 1, 2007.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 3009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
APDA. Basic Information About Parkinson's Disease. Jul. 14, 2008.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
Ash. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.
Autism Society of America. Incidence Numbers from Other Countries. www.autism-society.org. Accessed: Jul. 14, 2008.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barlow. A comparison of the blood pressure, kidney volume and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Belmonte et al. Fragile X syndrome and autism at the intersection of genetic and neural networks. Nat Neurosci. Oct. 2006; 9(10):1221-5 (abstract only).
Berg, et al. Section 10.5 Many Enzymes Are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.

(56) References Cited

OTHER PUBLICATIONS

Birnbaum, et al. Heat shock or stress proteins and their role as autoantigens in multiple sclerosis. Ann N Y Acad Sci. Dec. 19, 1997;835:157-67. Abstract only.

Blackmer. Parkinson disease: treatment and medication. Mar. 10, 2009., retrieved from the internet on Sep. 15, 2009, http://emedicine.medscape.com/article/312519-treatment.

Blog. Acid Phosphatase Research (blog). Acid-phosphatase.blogspot.com. 2008.

Bode et al. Usefulness of a simple photometric determination of chymotrypsin activity in stools-results of a multicentre study. Clin Biochem. 1986; 19:333-37.

Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.

Borowitz, et al. Use of pancreatic enzyme supplements for patients with cystic fibrosis in the context of fibrosing colonopathy. Consensus Committee. J Pediatr. Nov. 1995;127(5):681-4.

Boyd, et al. Positively charged amino acid residues can act as topogenic determinants in membrane proteins. Proc Natl Acad Sci U S A. Dec. 1989;86(23):9446-50.

Bradstreet, et al. Detection of Measles Virus Genomic RNA in Cerebrospinal Fluid of Children with Regressive Autism: a Report of Three Cases. J. Am Phys Surg. 2004; 9(2):38-45.

Brown. Background to Parkinson's Disease. biomed.brown.edu. Jul. 14, 2008.

Brudnak et al. Enzyme-based therapy for autism spectrum disorders—is it worth another look? Med Hypoth. 2002; 58:422-428.

Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.

Calderon-Garciduenas, et al. Immunotoxicity and environment: immunodysregulation and systemic inflammation in children. Toxicol Pathol. 2009;37(2):161-9.

Campbell et al. A genetic variant that disrupts MET transcription is associated with autism. Proc Natl Acad Sci USA. 2006; 103(45):16834-16839.

Campbell, et al. Distinct genetic risk based on association of MET in families with co-occurring autism and gastrointestinal conditions. Pediatrics. Mar. 2009;123(3):1018-24.

Carlton. Autism and malnutrition: the milk connection. Retrieved from the internet on Feb. 18, 2008, http://www.mercola.com/2004/autism_malnutrition.htm.

Caronna, et al. Autism spectrum disorders: clinical and research frontiers. Arch Dis Child. Jun. 2008;93(6):518-23.

Carroccio, et al. Pancreatic enzyme therapy in childhood celiac disease. A double-blind prospective randomized study. Dig Dis Sci. Dec. 1995;40(12):2555-60.

Carroccio, et al. Secondary impairment of pancreatic function as a cause of severe malabsorption in intestinal giardiasis: a case report. Am J Trop Med Hyg. Jun. 1997;56(6):599-602.

Carroccio, et al. Secretin-cerulein test and fecal chymotrypsin concentration in children with intestinal giardiasis. Int J Pancreatol. Oct. 1993;14(2):175-80.

Cassidy, et al. A new concept for the mechanism of action of chymotrypsin: the role of the low-barrier hydrogen bond. Biochemistry. Apr. 15, 1997;36(15):4576-84.

CDC. Attention-Deficit/Hyperactivity Disorder (ADHD). Www.cdc.org. 2005.

CDC. Autism Information Center/FAQs. Dept of Health and Human Services/CDC. Jan. 30, 2008.

CDC. High Blood Pressure. Division for Heart Disease Stroke Prevention. Jul. 15, 2003.

Chen, et al. Identification of two lysosomal membrane glycoproteins. J Cell Biol. Jul. 1985;101(1):85-95.

Chen, et al. Lysine 43 is trimethylated in subunit C from bovine mitochondrial ATP synthase and in storage bodies associated with batten disease. J Biol Chem. May 21, 2004;279(21):21883-7.

Cichoke, et al. The complete book of enzyme therapy. Penguin. 1998: 39, 42, 47, 50, and 53.

Claud, et a. Hypothesis: inappropriate colonization of the premature intestine can cause neonatal necrotizing enterocolitis. FASEB J. Jun. 2001;15(8):1398-403.

Commentary on the Japanese Pharmacopoeia, 14th ed., D929-D931, 2001.

Concerta. ADHD Myths and Facts. ADHD Myths and Facts about medication, girls, and symptoms and causes. Concerta.net. Jul. 15, 2008.

Corring, et al. Development of digestive enzymes in the piglet from birth to 8 weeks. I. Pancreas and pancreatic enzymes. Nutr Metab. 1978;22(4):231-43.

Couet, et al. Identification of peptide and protein ligands for the caveolin-scaffolding domain. Implications for the interaction of caveolin with caveolae-associated proteins. J Biol Chem. Mar. 7, 1997;272(10):6525-33.

Coyle. Treating the Negative Symptoms of Schizophrenia: An Expert Interview with Joseph Coyle, MD. www.narsad.org/?q=node/438/latest-research. 2006.

Craig, et al. Heat shock proteins: molecular chaperones of protein biogenesis. Microbiol Rev. Jun. 1993;57(2):402-14.

Croonenberghs, et al. Peripheral markers of serotonergic and noradrenergic function in post-pubertal, caucasian males with autistic disorder. Neuropsychopharmacology. Mar. 2000;22(3):275-83.

Cruse et al. Illustrated dictionary of immunology. CRC Press, New York. 1995.

Cuervo, et al. Cathepsin A regulates chaperone-mediated autophagy through cleavage of the lysosomal receptor. EMBO J. Jan. 2, 2003;22(1):47-59.

Darman. An introduction to alternative medicine for psychiactric conditions. Oct. 22, 2007, retrieved on Sep. 28, 2009, http://web.archive.org/web/20071022104238/http://altp[therapies4bipolar.info/ortho/html.

Dawe, et al. The chakragati mouse: a mouse model for rapid in vivo screening of antipsychotic drug candidates. Biotechnol J. Nov. 2007;2(11):1344-52.

Dawn. Autism: the Latest Prevalence Rates in USA—Now 1 in 175. Disabled Women's Network Ontario. Dawn.thot.net/autism2.html. 2006.

Dawson lab. Research Projects in Synthetic Protein Chemistry. 2005; 1-2.

Delong. News on Parkinson's. The Dana Foundation. Jul. 14, 2008.

Derwent. English abstract for RU 2286785 Nov. 10, 2006. Downloaded from the Derwent file Jul. 13, 2011.

Diaz-Hernandez, et al. Neuronal induction of the immunoproteasome in Huntington's disease. J Neurosci. Dec. 17, 2003;23(37):11653-61.

Digestive Enzyme Wikipedia. Retrieved from the internet Sep. 10, 2009, http://en.wikipedia.org/wiki/Digestive_enzyme.

Ding, et al. Proteasome inhibition in oxidative stress neurotoxicity: implications for heat shock proteins. J Neurochem. May 2001;77(4):1010-7.

Dobbs et al. Link between helicobacter pylori infection and idiopathic parkinsonism. Medical Hypothsis. 2000; 55(2):93-98.

Dockter et al. Determination of chymotrypsin in the feces by a new photometric method. Padiatr Padol. 1985; 20(3):257-265.

Edelson, et al. 3-Cyclohexene-1-glycine, an Isoleucine Antagonist. J. Am. Chem. Soc. 1958; 80(11):2698-2700.

Elkashef, et al. Biological markers of cocaine addiction: implications for medications development. Addict Biol. Jun. 2003;8(2):123-39.

Elphick, et al. Impaired luminal processing of human defensin-5 in Crohn's disease: persistence in a complex with chymotrypsinogen and trypsin. Am J Pathol. Mar. 2008;172(3):702-13.

Ethridge, et al. Acute pancreatitis results in induction of heat shock proteins 70 and 27 and heat shock factor-1. Pancreas. Oct. 2000;21(3):248-56.

Fafournoux, et al. Amino acid regulation of gene expression. Biochem J. Oct. 1, 2000;351(Pt 1):1-12.

Fallingborg, et al. Measurement of gastrointestinal pH and regional transit times in normal children. J Pediatr Gastroenterol Nutr. Aug. 1990;11(2):211-4.

(56) References Cited

OTHER PUBLICATIONS

Fallon. Could one of the most widely prescribed antibiotics amoxicillin/clavulanate "augmentin" be a risk factor for autism? Med Hypotheses. 2005;64(2):312-5.
Family Caregiver Alliance. Fact Sheet: Parkinson's Disease. Caregiver.org. Jul. 14, 2008.
Fernell, et al. No evidence for a clear link between active intestinal inflammation and autism based on analyses of faecal calprotectin and rectal nitric oxide. Acta Paediatr. Jul. 2007;96(7):1076-9.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 20/09 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May. 11, 2010 for U.S. Appl. No. 11/555,697.
Final Office Action dated Jun. 25, 2008 for U.S. Appl. No. 11/213,255.
Final Office Action dated Jul. 2, 1010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Fitzsimmons, et al. High-dose pancreatic-enzyme supplements and fibrosing colonopathy in children with cystic fibrosis. N Engl J Med. May 1, 1997;336(18):1283-9.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in E. coli stimulates transcription of Ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
Health.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
Hitti. Allergy, celiac disease, and ileal lymphonodular. WebMD. 2005. 1-2.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Horvath et al. Improved social and language skills after secretin administration in patients with autistic spectrum disorders. Journal of the Association for Academic Minority Physicians. Jan. 1998; 9(1):9-15.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in

(56) References Cited

OTHER PUBLICATIONS children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Kearney, et al. Global burden of hypertension: analysis of worldwide data. Lancet. Jan. 15-21, 2005;365(9455):217-23. Abstract only.
Knivsberg, et al. A randomised, controlled study of dietary intervention in autistic syndromes. Nutr Neurosci. Sep. 2002;5(4):251-61.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of helocobacter pylori. Acta Gastro-Enterologica Belgica. 2000; 63(4):388-392.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Larimore. How Common Is ADHD? Facts About ADHD. Jul. 15, 2008.
Lashkari, et al. Williams-Beuren syndrome: An update and review for the primary physician. Clinical Pediatrics. 1999; 38(4):189-208.
Layer et al. Pancreatic enzyme replacement therapy. Current Gastroenterology Reports. 2001; 3:101-108.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacFabe, et al. Neurobiological effects of intraventricular propionic acid in rats: possible role of short chain fatty acids on the pathogenesis and characteristics of autism spectrum disorders. Behav Brain Res. 2006;176(1):149-69.
MacReady. Parkinson's Diseasne Treatment: what you should know. Retrieved from the internet on Sep. 15, 2009, http://www.everydayhealth.com/parkinsons-disease-treatment-overview.aspx.

Mannino, et al. Surveillance for asthma—United States, 1960-1995. MMWR CDC Surveill Summ. Apr. 24, 1998;47(1):1-27.
Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-Compulsive Disorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McAlonan, et al. Brain anatomy and sensorimotor gating in Asperger's syndrome. ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Medsafe. Data sheet for alpha-lactose, Jul. 21, 2008, http://www.medsafe.govt.nz/Profs/Datasheet/a/Alphalactulosesyrup.htm.
Medscape. Burden of Hypertension in the United States Greater Than Ever. www.medscape.com. Jul. 14, 2004.
Melmed, et al. Metabolic markers and gastrointestinal symptoms in children with autism and related disorders. J Pediatr Gast Nutr. 2000; 31:S31-S32. Abstract only.
Merck. Autism, Merck manual online medical library home addition, retrieved from the internet Mar. 10, 2008, http://www.mercl.com/mmhge/sec23/ch286/ch286b.html.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michell et al. Biomarkers and parkinson's disease. Brain. 2004; 127(8):1693-1705.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Munasinghe et al. Digestive enzyme supplementation for autism spectrum disorders: a double-blind randomized controlled trial. J Autism Dev Disord. Sep. 2010;40(9):1131-8.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56 ,58, 60, 64.

(56) References Cited

OTHER PUBLICATIONS

Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 2012 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.
Notice of Allowance dated Mar. 21, 2012 for U.S. Appl. No. 12/487,864.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of Allowance dated Apr. 15, 2011 for U.S. Appl. No. 12/487,868.
Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23. 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.
Notice of allowance dated Dec. 23, 2015 for U.S. Appl. No. 12/493,122.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
O'Connell. Hypertension Guide. cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 13, 2016 for U.S. Appl. No. 14/612,604.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 2011 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 17, 2015 for U.S. Appl. No. 13/733,873.
Office action dated Jul. 18, 2012 for U.S. Appl. No. 12/047,818.

(56) References Cited

OTHER PUBLICATIONS

Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.
Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office Action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Nov. 21, 2014 for U.S. Appl. No. 13/926,822.
Office Action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office Action dated Jan. 21, 2011 for U.S. Appl. No. 12/386,051.
Office Action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office Action dated Dec. 24, 2015 for U.S. Appl. No. 13/757,412.
Office Action dated Jan. 29, 2002 for U.S. Appl. No. 09/707,395.
Office Action dated Jan. 8, 2010 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 3002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Office Action dated May 11, 2016 U.S. Appl. No. 14/713,242.
Owley, et al. Multisite, double-blind, placebo-controlled trial of porcine secretin in autism. J Am Acad Child Adolesc Psychiatry. Nov. 2001;40(11):1293-9.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Pdtalks. Motivational & Inspirational Speaking From a Parkinson's Patient Perspective. pdtalks.com/Parkinson_s_Disease.html. Jul. 14, 2008.
Perman et al. Role of ph in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Remtulla et al. Stool chymotrypsin activity measured by a spectrophotometric procedure to identify pancreat disease in infants. Clinical Biochemistry. Dec. 1986; 19:341-342.

(56) References Cited

OTHER PUBLICATIONS

Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Revolution health. Enzyme therapy. revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Rubenstein, et al. Model of autism: increased ratio of excitation/inhibition in key neural systems. Genes Brain Behav. Oct. 2003;2(5):255-67.
Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.
Sahelian. Enzymes. raysahelian.com/enzymes.html. Sep. 2, 2008.
Sandler, et al. Lack of benefit of a single dose of synthetic human secretin in the treatment of autism and pervasive developmental disorder. N Engl J Med. Dec. 9, 1999;341(24):1801-6.
Sandler et al. Short term benefit from oral vancomycin treatment of regressive-onset autism. J of Child Neuro. 2000; 15(7):42-435.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influecing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:I17-25.
Seneca et al. Enhancement of brain 1-dopa concetration with a-chymotrypsm. J American Geriatrics Society. 1973; 256-258. Abstract only.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Shelby, et al. Enzymatic debridement with activated whole pancreas. American Journal of Surgery. Oct. 1958; 96(4):545-549.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.
Skeels et al. Crytosporidium infection in Oregon public health clinic patients 1985-88: the value of statewide laboratory surveillance. AJPH. 1990; 80(3):305-308.
Smith, et al. Fecal chymotrypsin and trypsin determinations. Canadian Medical Association Journal. 1971; 104(8):691-4 and 697.
Statemaster. Number of Children with Autism (most recent) by state. Statemaster.com Jul. 14, 2008.
Statemaster. Number of Children with Autism (most recent w/graph) by state. Statemaster.com Jul. 14, 2003.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Supplemental Amendment and Response dated Jun. 8, 2010 to Restriction Requirement dated Oct. 7, 2009 for U.S. Appl. No. 12/283,090.
Tager-Flusberg, et al. Language disorders: autism and other pervasive developmental disorders. Pediatr Clin North Am. Jun. 2007;54(3):469-81, vi.
Terrie, et al. Understanding Pancreatic Enzyme Products. Dec. 15, 2008.

(56) References Cited

OTHER PUBLICATIONS

The Alzheimer's Association. Basics of Alzheimer's Disease. 2005, 32 pages. http://www.alz.org/national/documents/brochure_Basicsofalz_low/pdf.

Thefreedictionary. Term Sprinkles. Www.thefreedictionary.com. Accessed Nov. 2, 2011. 1 page.

Thomas, et al. Defective protein folding as a basis of human disease. Trends Biochem Sci. Nov. 1995;20(11):456-9.

Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.

Torrente, et al. Focal-enhanced gastritis in regressive autism with features distinct from Crohn's and Helicobacter pylori gastritis. Am J Gastroenterol. Apr. 2004;99(4):598-605.

Torrente, et al. Small intestinal enteropathy with epithelial IgG and complement deposition in children with regressive autism. Mol Psychiatry. 2002;7(4):375-82, 334.

Tran, et al. Treatment of complex regional pain syndrome: a review of the evidence. Can J Anaesth. Feb. 2010;57(2):149-66.

Trauner, et al. Specific cognitive deficits in young children with cystinosis: evidence for an early effect of the cystinosin gene on neural function. J Pediatr. Aug. 2007;151(2):192-6.

Tsan, et al. Heat shock proteins and immune system. J Leukoc Biol. Jun. 2009;85(6):905-10.

Tsang et al. Extragastroduodenal conditions associated with Heliobacter pylori infection. Hong Kong Medical Journal. 1999; 5(2):169-174.

Uhlmann, et al. Potential viral pathogenic mechanism for new variant inflammatory bowel disease. Mol Pathol. Apr. 2002;55(2):84-90.

Unis, et al. A randomized, double-blind, placebo-controlled trial of porcine versus synthetic secretin for reducing symptoms of autism. J Am Acad Child Adolesc Psychiatry. Nov. 2002;41(11):1315-21.

UPI. Number of autistic Calif. students triples. United Press International. Jul. 12, 2008.

U.S. Appl. No. 13/502,989 Notice of Allowance dated Aug. 10, 2016.

"U.S. Appl. No. 13/705,763 Final Office Action dated May 24, 2016".

"U.S. Appl. No. 14/640,385 Supplemental Notice of Allowability dated May 26, 2016".

U.S. Appl. No. 15/074,115, filed Mar. 18, 2016.
U.S. Appl. No. 15/089,842, filed Apr. 4, 2016.
U.S. Appl. No. 13/002,136, filed Dec. 30, 2010.
U.S. Appl. No. 13/144,286, filed Jul. 12, 2011.
U.S. Appl. No. 13/144,290, filed Jul. 12, 2011.
U.S. Appl. No. 13/204,881, filed Aug. 8, 2011.
U.S. Appl. No. 13/208,963, filed Aug. 12, 2011.
U.S. Appl. No. 13/271,783, filed Oct. 12, 2011.
U.S. Appl. No. 13/313,629, filed Dec. 7, 2011.
U.S. Appl. No. 13/313,708, filed Dec. 7, 2011.
U.S. Appl. No. 13/407,408, filed Feb. 28, 2012.
U.S. Appl. No. 13/448,061, filed Apr. 16, 2012.
U.S. Appl. No. 13/481,087, filed May 25, 2012.
U.S. Appl. No. 13/502,989, filed Apr. 19, 2012.
U.S. Appl. No. 13/503,844 , filed Apr. 24, 2012.
U.S. Appl. No. 13/562,999, filed Jul. 31, 2012.
U.S. Appl. No. 13/705,763, filed Dec. 5, 2012.
U.S. Appl. No. 13/733,873, filed Jan. 3, 2012.
U.S. Appl. No. 13/737,225, filed Jan. 9, 2012.
U.S. Appl. No. 13/757,412, filed Feb. 1, 2013.
U.S. Appl. No. 13/836,135, filed Mar. 15, 2013.
U.S. Appl. No. 13/926,822, filed Jun. 25, 2013.
U.S. Appl. No. 14/007,793, filed Sep. 26, 2013.
U.S. Appl. No. 14/037,652, filed Sep. 26, 2013.
U.S. Appl. No. 14/037,696, filed Sep. 26, 2013.
U.S. Appl. No. 14/087,930, filed Nov. 22, 2013.
U.S. Appl. No. 14/296,091, filed Jun. 4, 2014.
U.S. Appl. No. 14/528,715, filed Oct. 30, 2014.
U.S. Appl. No. 14/612,580, filed Feb. 3, 2015.
U.S. Appl. No. 14/612,604, filed Feb. 3, 2015.
U.S. Appl. No. 14/639,425, filed Mar. 5, 2015.
U.S. Appl. No. 14/640,385, filed Mar. 6, 2015.
U.S. Appl. No. 14/921,896, filed Oct. 23, 2015.
U.S. Appl. No. 14/612,580 Office Action dated Dec. 24, 2015.
USP (32)-NF(27) 2009, Pancreatin, V.3, pp. 3194-3195.

Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.

Vargas, et al. Neuroglial activation and neuroinflammation in the brain of patients with autism. Ann Neurol. Jan. 2005;57(1):67-81.

Vellard. The enzyme as drug: application of enzymes as pharmaceuticals. Curr Opin Biotechnol. Aug. 2003;14(4):444-50.

Vilanova, et al. Preparative isolation of the two forms of pig pancreatic pro-(carboxypeptidase A) and their monomeric carboxypeptidases A. Biochem J. Aug. 1, 1985;229(3):605-9.

Vojdani, et al. Antibodies against CNS antigens in autism: Possible cross-reaction with dietary proteins and infectious agent antigens. Neuropsychiatric Disorders and Infection. 2004; 19:171-186.

Vojdani, et al. Heat shock protein and gliadin peptide promote development of peptidase antibodies in children with autism and patients with autoimmune disease. Clin Diagn Lab Immunol. May 2004;11(3):515-24.

Vojdani, et al. Immune response to dietary proteins, gliadin and cerebellar peptides in children with autism. Nutr Neurosci. Jun. 2004;7(3):151-61.

Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.

Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.

Wakefield. Autistic enterocolitis: is it a histopathological entity? Histopathology. 2006; 1-5.

Wakefield. Enterocolitis, Autism, and Measles Virus. Consensus in Child Neurology: Biological Bases and Climical Perspectives in Autism. 2002; 74-81.

Wakefield, et al. Enterocolitis in children with developmental disorders. Am J Gastroenterol. Sep. 2000;95(9):2285-95.

Wakefield, et al. Ileal-lymphoid-nodular hyperplasia, non-specific colitis, and pervasive developmental disorder in children. Lancet. Feb. 28, 1998;351(9103):637-41.

Wakefield, et al. Review article: the concept of entero-colonic encephalopathy, autism and opioid receptor ligands. Aliment Pharmacol Ther. Apr. 2002;16(4):663-74.

Wakefield, et al. The significance of ileo-colonic lymphoid nodular hyperplasia in children with autistic spectrum disorder. Eur J Gastroenterol Hepatol. Aug. 2005;17(8):827-36.

Wakefield. The gut-brain axis in childhood developmental disorders. J Pediatr Gastroenterol Nutr. May-Jun. 2002;34 Suppl 1:S14-7.

Walsh, et al. Heat shock and the role of the HSPs during neural plate induction in early mammalian CNS and brain development. Cell Mol Life Sci. Feb. 1997;53(2):198-211.

Walsh, et al. Reduced violent behavior following chemical therapy. Physiology and behavior. 2004; 82:835-839.

Wang, et al. Activation of Ras/Erk pathway by a novel MET-interacting protein RanBPM. J Biol Chem. Sep. 27, 2002;277(39):36216-22.

WE MOVE, PD Workbook, The WEMOVE Clinician's Guide to Parkinson's Disease, 2006.

Weintraub, et al. Morphometric studies of pancreatic acinar granule formation in NCTR-Balb/c mice. J Cell Sci. May 1992;102 ( Pt 1):141-7.

Welch, et al. Brain effects of chronic IBD in areas abnormal in autism and treatment by single neuropeptides secretin and oxytocin. J Mol Neurosci. 2004;25(3):259-74.

(56) References Cited

OTHER PUBLICATIONS

Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
Yahoo!.com. Who is affected by Parkinson's disease. Yahoo! Health. Jul. 14, 2008.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zhang et al. Lactulose-mannitol intestinal permeability test in children with diarrhea caused by rotavirus abd cryptosporidium. J of Pediatric Gastro & Nutrition. 2000; 31(1):16-21.
Alexrod FB et al. Hereditary sensory an autonomic neuropathies: types II, III and IV. Orphanet Journal of Rare Diseases, 2:39 (2007).
Anderson, George M., et al. Determination of serotonin in whole blood, platelet-rich plasma, platelet-poor plasma and plasma ultrafiltrate. Life Sciences 40(11):1063-1070 (Mar. 16, 1987) [Abstract Only].
Arnold, GL et al. Plasma amino acids profiles in children with autism: potential risk of nutritional deficiencies. J. Autism Dev. Disord. 33(4):449-454 (Aug. 2003) [Abstract Only].
Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).
Beliaev, O.A. The therapeutic efficacy of the triase preparation in experimental pancreatic exocrine insufficiency. Eksp Lin Farmakiol. 57:38-40 (1994) (Abstract Only—English Translation).
Block, et al. A rapid food screener to assess fat and fruit and vegetable intake. Am J Prev Med. May 2000;18(4):284-8.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Borowitz et al., Study of a novel pancreatic enzyme replacement therapy in pancreatic insufficient subjects with cystic fibrosis J.Pediatr., 149:658-662 (2006).
Bouhnik, et al. Lactulose ingestion increases faecal bifidobacterial counts: A randomized double-blind study in healthy humans. European Journal of Clinical Nutrition 58:462-466 (2004).
Bowen. Exocrine secretions of the pancreas. Jul. 5, 2006. Accessed online at www.vivo.colostate.edu/hbooks/pathphys/digestion/pancreas/exocrine.html.
Bray, et al. Effect of dietary protein content on weight gain, energy expenditure, and body composition during overeating. A randomized controlled trial. JAMA. Jan. 4, 2012; 307(1):47-55.
Brinkley, et al. Factor analysis of the aberrant behavior checklist in individuals with autism spectrum disorders. J Autism Dev Disord. Nov. 2007;37(10):1949-59. Epub Dec. 21, 2006.
Brudnak, Mark et al., Guide to intestinal health in autism spectrum disorder, Kirkman Laboratories, (Oct. 2001).

Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
Chaignon et al. Susceptibility of staphylococcal biofilms to enzymatic treatments depends on their chemical compositions. Appl. Microbiol. Appl. Microbiol. 75:125-132 (2007).
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Childhood Autism Rating Scale (CARS), Wikipedia, downloaded May 5, 2014.
Cichoke. Celiac disease. The complete book of enzyme therapy. Penguin. New York, NY. 1999; 174-177.
Cichoke. Influenza. In: The Complete Book of Enzyme Therapy. D. Stewart, ed. Copyright 1999. Anthony J. Cichoke. Penguin Putnam, Inc., New York, New York. pp. Contents, 50, 273-275 and 455.
Co-pending U.S. Appl. No. 15/840,883, filed Dec. 13, 2017.
Co-pending U.S. Appl. No. 16/103,192, filed Aug. 14, 2018.
Coutinho, AM et al. Variants of the serotonin transporter gene (SLC6A4) significantly contribute to hyperserotonemia in autism. Mol Psychiatry. Mar. 2004;9(3):264-71.
Creon digestive enzymes. Celic.com/ Jun. 2009. http://www.celiac.com/gluten-free/topic/59195-creon-digestive-enzymes.
Creon. Full prescribing information. Last edited Mar. 2013. Abbvie Inc 2012. www.rxabbvie.com/pdf/creon_PI.pdf.
Curemark press release. Curemark Receives Investigational New Drug Clearance for CM-AT for Autism. Mar. 26, 2009. http://www.medicalnewstoday.com/releases/143723.php.
Dajcs, et al. Lysostaphin is effective in treating methicillin-resistant *Staphylococcus aureus* endophthalmitis in the rabbit. Curr Eye Res. Jun. 2001;22(6):451-7.
Digestive Enzyme Preparation: Pancreatin listed in Japanese Pharmacopoeia, Aug. 2008,<URL:http:>(in Japanese with English translation)</URL:http:>.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Dupiereux, et al. Creutzfeldt-Jakob, Parkinson, lewy body dementia and Alzheimer diseases: from diagnosis to therapy. Cent Nerv Syst Agents Med Chem. Mar. 2009;9(1):2-11.
Eaves, et al. The criterion-related validity of the Childhood Autism Rating Scale and the Autism Behavior Checklist. J Abnorm Child Psychol. Oct. 1993;21(5):481-91. abstract only.
Emc, Creon 10000 Capsules, May 18, 2015, Available Online at: www.medicines.org.uk/emc/medicine/2068.
EMedExpert, Antibiotics: Cephalosporins, Available online at: http://www.emedexpert.com/compare/ cephalosporins.shtml, available as early as Jun. 2, 2007 per Internet Archive Wayback Machine.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Exocrine Pancreatic Insufficiency (Enzymes) Document downloaded online on Jan. 8, 2016 at: http://www.epi4dogs.com/enzyme.htm< http:></http:>.
Fafournoux, P. et al. Amino acid regulation of gene expression. Biochemical Journal, 351:1-12(2000).
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.

(56) References Cited

OTHER PUBLICATIONS

Fliri, et al. Drug effects viewed from a signal transduction network perspective. J Med Chem. Dec. 24, 2009;52(24):8038-46. doi: 10.1021/jm901001p.

Frossard, et al. Both thermal and non-thermal stress protect against caerulein induced pancreatitis and prevent trypsinogen activation in the pancreas. Gut. Jan. 2002;50(1):78-83.

Girella, E. et al. The assay of chymotrypsin in stool as a simple and effective test of exocrine pancreatic activity in cystic fibrosis. Pancreas, 3(3):254-262 (1988).

GM Chemie 2010 Products: Hypromellose Phthalate accessed from www.gmchemie.com on Sep. 22, 2014.

Hamel, E. et al. Effects of Cocaine on Rat Pancreatic Enzyme Secretion and Protein Synthesis, Digestive Diseases, 23(3):264-268 (Mar. 1978).

Holquist et al. FDA safety page Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.

Holten, et al. Appropriate prescribing of oral beta-lactam antibiotics. Am Fam Physician. Aug. 1, 2000;62(3):611-20.

Information of Papain from Worthington Enzymes webpage http://www.worthington-biochem.com/pap/default.html Downloaded Jan. 17, 2013.

International Application No. PCT/US18/26841 International Search Report and Written Opinion dated Jul. 3, 2018.

International preliminary report on patentability dated Jul. 17, 2014 for PCT/US2013/020183.

International search report and written opinion dated Feb. 21, 2013 for PCT/US2013/020183.

International search report and written opinion dated May 9, 2013 for PCT/US2013/024453.

International search report and written opinion dated Aug. 27, 2013 for PCT/US2013/043444.

International search report and written opinion dated Nov. 12, 2012 for PCT/US2012/034489.

International search report and written opinion dated Mar. 5, 2010 for PCT/US2010/020259.

Kidd, P.M., Autism, an extreme challenge to integrative medicine. Part 2: medical management. Altern. Med. Rev., 7(6):172-499 (Dec. 2002).

King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
MacDonald. Thyrotoxicosis treated with pancreatic extract and iodine. Lancet. 1943; 244(6251):788.
Marion et al., A New Procedure Allowing the Complete Removal and Prevention of Hemodialysis. Blood Purification, 23:339-348 (2005).
Matikainen, et al. Autonomic dysfunction in long-standing alcoholism. Alcohol. 1986;21(1):69-73. Abstract only.
Merriam-Webster 2014 Definition: Precipitate accessed from www.mirriam-webster.com on Sep. 22, 2014.
Millipore EMD catalog (online). Papain, unit definition, EMD Millipore Corp, 2013. Downloaded May 13, 2013.
Mitsui, et al. Role of aminopeptidases in the blood pressure regulation. Biological and Pharmaceutical Bulletin of Japan, Pharmaceutical Society of Japan. 2004; 27(6):768-771.
Nestler, et al. Delta-FosB: A sustained molecular switch for addiction. PNAS 98(20): 11042-11046 (Sep. 25, 2001).
Neumeyer, Ann. M. et al. Brief Report: Bone Fractures in Children and Adults with Autism Spectrum Disorders. J. Autism Dev. Disord. 45(3):881-887 (Mar. 2016).
NIH, Celiac Disease, National Digestive Diseases Information Clearinghouse: Bethesda, MD, 2008; 12 pages.
No Author. RSDSA, 2015: Telltale signs and symptoms of CRPS/RSD on the web at rsds.org/telltale-signs-and-symptoms-of-crpsrsd. [Accessed: Sep. 5, 2018].
Okahata, et al. Lipid-coated enzymes as efficient catalysts in organic media. Trends in Biotechnology. 1997; 15(2):50-54.
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Olivar-Parra, et al. Training referential communicative skills to individuals with autism spectrum disorder: a pilot study. Psychological Reports. 2011; 109:921-939.
Pancrease. Patient information leaflet. Pancrease HL Capsules. Last updated Apr. 30, 2013. Janssen-cilag LTD. www.medicines.org.uk/EMC/medicine/7326.
Pancreatin 8X USP Powder. Product Specification. Jul. 2000. In: Product Manual. American Laboratories Incorporated. Omaha, NE. p. 1.
Patel, et al. Formulation and evaluation of mucoadhesive glipizide microspheres. AAPS PharmSciTech. 2005; 6(1):E49-E55.
Petrolatum: Pharmaceutical Excipients. London: Pharmaceutical Press. 2006. 1-6.
Felig, P. Amino acid metabolism in man. Annual Review of Biochemistry, 44(1):933-955 (1975). [Abstract Only].
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
Chez, M. et al. Secretin and autism: a two-part clinical investigation. Journal of Autism and Developmental Disorders, 30(2), 87-94 (Apr. 2000) [Abstract Only].
Evans, C. et al. Altered amino acid excretion in children with autism. Nutritional Neuroscience, 11(1):9-17 (Feb. 2008).
First, M.Structured clinical interview for DSM-IV-TR axis I disorders, research version, patient edition. (SCID-I/P) New York: Biometrics Research, New York State Psychiatric Institute. (2002).
Guesnet, P. et al. Docosahexaenoic acid (DHA) and the developing central nervous system (CNS)—Implications for dietary recommendations. Biochimie, 93(1):7-12(2011). [Abstract Only].
Heil, M., et al. Low endogenous fecal chymotrypsin: a possible biomarker for autism. Poster presented at the annual IMFAR Conference on Autism, Atlanta, GA.(May 2014) p. 1.
Matthews, D. Intestinal absorption of amino acids and peptides. Proceedings of the Nutrition Society, 31(2):171-177(1972).
McClung, C.A. et al. DeltaFosB: A molecular switch for long-term adaptation in the brain. Molecular Brain Research, 132(2):146-154 (Dec. 20, 2004).
Morimoto, R. The heat shock response: Systems biology of proteotoxic stress in aging and disease. Cold Spring Harbor Symposia on Quantitative Biology, 76:91-99 (2011) (Epub: Feb. 27, 2012).
Munasinghe, S.A. et al. Digestive enzyme supplementation for autism spectrum disorders: A double-blind randomized controlled trial. Journal of Autism and Developmental Disorders, 40(9):1131-1138 (Sep. 2010) [Abstract Only].
Naushad, Shaik Mohammad et al. Autistic children exhibit distinct plasma amino acid profile. Indian Journal of Biochemistry and Biophysics, 50(5):474-478 (Oct. 2013).
Robinson, T. et al. Incentive-sensitization and addiction. Addiction, 96(1):103-114 (Jan. 2001).
Schedl, H. et al. Absorption of l-methionine from the human small intestine. Journal of Clinical Investigation, 47(2): 417-425 (1968).

(56) References Cited

OTHER PUBLICATIONS

Regan, et al. Comparative effects of antacids, cimetidine and enteric coating on the therapeutic response to oral enzymes in severe pancreatic insufficiency. N Engl J Med. Oct. 20, 1977;297(16):854-8.
Rivest, J. et al. A dynamic model of protein digestion in the small intestine of pigs. Journal of Animal Science, 78(2):328-240 (Feb. 2000).
Roxas, et al. Colds and influenza: a review of diagnosis and conventional, botanical, and nutritional considerations. Alternative Medicine Review. 2007; 12(1):25-48.
Schizophreniform disorder. Merck Manuals Online Medical Library. Nov. 2005. (in Japanese with English translation).
Seltzer, et al. The Symptoms of Autism Spectrum Disorders in Adolescence and Adulthood. Journal of Autism and Developmental Disorders. 2003; 33(6):565-581.
Serna, et al. Pathogenesis and treatment of Shiga toxin-producing *Escherichia coli* infections. Curr Opin Gastroenterol. Jan. 2008;24(1):38-47.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Singh, Manjit. Alcoholic pancreatitis in rats fed ethanol in a nutritionally adequate liquid diet. International Journal of Pancreatology, 2:311-324 (1987).
Skinner, et al. Treatment of Prion Disease with Heterologous Prion Proteins. PLoS One. Jul. 2, 2015;10(7):e0131993. doi: 10.1371/journal.pone.0131993. eCollection 2015.
Avruch, J., et al. Amino acid regulation of TOR complex 1. AJP: Endocrinology and Metabolism, Am. J. Physiol. Endocrinol. Metab. 296(4):E592-E602 (Apr. 2009).
Daly, E., et al. Response inhibition and serotonin in autism: A functional MRI study using acute tryptophan depletion. Brain, 137(9), 2600-2610 (Sep. 2014).
Drabkin, H., et al. Initiation of protein synthesis in mammalian cells with codons other than AUG and amino acids other than methionine. Molecular and Cellular Biology, 18(9): 5140-5147 (Sep. 1998).
Fairclough, P. et al. Comparison of the absorption of two protein hydrolysates and their effects on water and electrolyte movements in the human jejunum. Gut, 21(10):829-834 (1980).
McClung, C., et al. Regulation of gene expression and cocaine reward by CREB and DeltaFosB. Nature Neuroscience, 6(11):1208-1215 (2003). [Abstract Only].
Nestler, E.J. Molecular basis of long-term plasticity underlying addiction. Nature Reviews Neuroscience, 2(2):119-128 (Feb. 2001).
Norton, L. et al. Leucine regulates translation initiation of protein synthesis in skeletal muscle after exercise. The Journal of Nutrition, 136(2):533S-537S (Feb. 2006).
Schain, RJ et al. Studies on 5-hydroxyindole metabolism in autistic and other mentally retarded children. J. Pediatr. 58:315-320 (1961) [Summary Only].
Tang, G. et al. Loss of mTOR-dependent macroautophagy causes autistic-like synaptic pruning deficits. Neuron, 83(5):1131-1143 (Sep. 3, 2014).
Williams, K. et al. Cochrane Review: Selective serotonin reuptake inhibitors (SSRIs) for autism spectrum disorders (ASD). Evidence-Based Child Health: A Cochrane Review Journal, 6(4):1044-1078 (Jul. 2011). [Abstract Only].
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Sundstrom, et al. A deadly prion disease: fatal familial insomnia. J Neurosci Nurs. Dec. 2003;35(6):300-5. Abstract only.
Swayne, et al. Pathobiology of H5N2 Mexican avian influenza virus infections of chickens. Vet Pathol. Nov. 1997;34(6):557-67.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
Troy. Pancreatic Enzymes. Remington: The Science and Practice of Pharmacy, 21st edition. Lippincot Williams & Wilkins, 2006. p. 1304.
Tuohy, K.M. et al. Using probiotics and prebiotics to improve gut health. Reviews, Therapeutic Focus, DDT 8(15) Aug. 2003.
UK search and examination report dated Mar. 26, 2013 for GB 1111565.6.
UK search and examination report dated Mar. 27, 2013 for GB 1111566.4.
UK search and examination report dated Apr. 18, 2013 for GB 1117669.0.
U.S. Appl. No. 12/054,343 Non-Final Office Action dated Dec. 26, 2017.
U.S. Appl. No. 12/535,676 Non-Final Office Action dated Sep. 6, 2018.
U.S. Appl. No. 12/786,739 Final Office Action dated Jun. 23, 2017.
U.S. Appl. No. 12/786,739 Final Office Action dated Sep. 25, 2018.
U.S. Appl. No. 12/786,739 Non-Final Office Action dated Jan. 4, 2018.
U.S. Appl. No. 13/002,136 Advisory Office Action dated Jul. 9, 2018.
U.S. Appl. No. 13/002,136 Final Office Action dated Jan. 8, 2018.
U.S. Appl. No. 13/503,844 Final Office Action dated Nov. 30, 2017.
U.S. Appl. No. 13/733,873 Final Office Action dated Feb. 21, 2018.
U.S. Appl. No. 13/757,412 Final Office Action dated Sep. 12, 2017.
U.S. Appl. No. 13/836,135 Non-Final Office Action dated Mar. 15, 2018.
U.S. Appl. No. 14/296,091 Final Office Action dated Aug. 23, 2017.
U.S. Appl. No. 14/296,091 Final Office Action dated Oct. 1, 2018.
U.S. Appl. No. 14/296,091 Non-Final Office Action dated Mar. 22, 2018.
U.S. Appl. No. 14/612,580 Final Office Action dated Aug. 10, 2017.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/713,221 Notice of Allowance dated Oct. 19, 2017.
U.S. Appl. No. 14/713,242 Final Office Action dated Jul. 21, 2017.
U.S. Appl. No. 14/713,242 Non-Final Office Action dated Mar. 29, 2018.
U.S. Appl. No. 14/921,896 Final Office Action dated Jan. 25, 2018.
U.S. Appl. No. 14/921,896 Notice of Allowability dated Sep. 12, 2018.
U.S. Appl. No. 14/921,896 Notice of Allowance dated Jul. 18, 2018.
U.S. Appl. No. 15/089,842 Non-Final Office Action dated Jun. 26, 2018.
U.S. Appl. No. 15/089,842 Office Action dated Dec. 8, 2017.
U.S. Appl. No. 15/164,493 Non-Final Office Action dated Feb. 27, 2018.
U.S. Appl. No. 15/185,511 Notice of Allowance dated Nov. 16, 2017.
U.S. Appl. No. 15/265,415 Non-Final Office Action dated Apr. 11, 2018.
U.S. Appl. No. 15/265,620 Non-Final Office Action dated Jun. 20, 2018.
U.S. Appl. No. 15/593,121 Non-Final Office Action dated Mar. 8, 2018.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
Wisniewski, et al. Therapeutic approaches for prion and Alzheimer's diseases. FEBS J. Aug. 2007;274(15):3784-98. Epub Jul. 6, 2007.
Wolfson, D., Making sense of digestive enzymes, Klaire Labs, Mar. 13, 2006.
Xu. Pancreatin therapy in chronic pancreatitis. Clin J Dig, May 2005; 25(5):313-315. (in Chinese with English translation).
Yang, Xinyi et al. Advances in anti-staphylococcal agent lysostaphin. Chinese Journal of New Drugs 14(9):1113-1117 (2005).
American Family Physician. Cuts, Scrapes, and Stitches. Am Fam Physician 69(11):2647-2648 (Jun. 1, 2004).

(56) References Cited

OTHER PUBLICATIONS

Bhattacharjee et al., Treatment of Pancreatic Exocrine Insufficiency with Enteric Coated Pancreatin Formulations: An Overview. International Journal of Pharmaceutical Sciences and Nanotechnology. 6(3):2125-2130 (2013).

Carroccio et al. Effectiveness of Enteric-coated Preparations on Nutritional Parameters in Cystic Fibrosis. Digestion 41:201-206 (1988).

Cornish. A balanced approach towards healthy eating in autism, Journal of Human Nutrition and Dietetics 11:501-509 (1998).

Flament, M.P. et al. Develoment of 400 μm Pellets by Extrusion-Spheronization Application with Gelucire 50/02 to Produce a "Srinkle" Form, Drug Develoment and industrial Pharmacy, 30:1, 43-51, DOI: 10.1081/DDC-120027510 (2004).

Ijuin, H. Evaluation of pancreatic exocrine function and zinc absorption in alcoholism. The Kurume Medical Journal 45.1 (1998): 1-5.

Keller, et al. Pancreatic enzyme supplementation therapy. Current Treatment Options in Gastroenterology 6.5 (2003): 369-374.

Koh et al. Inflammation and wound healing: The role of the macrophage. Expert Rev Mol Med. 13:e23 (Author manuscript), 2011.

Koivu et al. Determination of Phylloquinone in Vegetables, Fruits, and Berries by High-Performance Liquid Chromatography with Electrochemical Detection. J. Agric. Food Chem. 45(12):4644-4649 (1997).

Medori et al. Fatal Familial Insomnia, A Prion Disease With a Mutation at Condon 178 of The Prion Protein Case. N Engl J Med 326:444-449 (1992).

Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.

Patton, J. et al. Factor structure of the barratt impulsiveness scale. Journal of Clinical Psychology, 51(6): 768-774 (Nov. 1995).

P.Ya. Grigoryev et al., Reference Guide on Gastroenterology, Moscow, MIA-2003, pp. 454,460,465.

Qi, et al. Solubility and emulsifying properties of soy protein isolates modified by pancreatin. Journal of Food Science 62.6 (1997): 1110-1115.

Salpekar, et al. Bipolar Spectrum Disorder Comorbid With Autism Spectrum Disorder; NADD Bulletin, vol. X, 2007. No. 6, Article 1, pp. 1-5, downloaded from http://www.thenadd.org/nadd-bulletin/archive/volunne-x/ on Dec. 11, 2018.

Diagnostic and Statistical Manual of Mental Disorders, Fourth Edition, Primary Care Version, Chapter 6, American Psychiatric Association (2000).

Diagnostic and Statistical Manual of Mental Disorders, Fourth Edition, Text Revision, DSM-IV-TR, American Psychiatric Association (2000).

U.S. Appl. No. 15/840,883 Office Action dated Aug. 8, 2019.
U.S. Appl. No. 16/010,850 Restriction Requirement dated Jun. 21, 2019.
U.S. Appl. No. 16/103,192 Restriction Requirement dated Aug. 9, 2019.
U.S. Appl. No. 13/002,136 Non-Final Office Action dated Dec. 18, 2018.
U.S. Appl. No. 13/757,412 Office Action dated Apr. 16, 2019.
U.S. Appl. No. 13/836,135 Final Office Action dated Dec. 14, 2018.
U.S. Appl. No. 13/836,135 Notice of Allowance dated Apr. 25, 2019.
U.S. Appl. No. 14/713,242 Final Office Action Jan. 9, 2019.
U.S. Appl. No. 15/089,842 Final Office Action dated Dec. 4, 2018.
U.S. Appl. No. 15/164,493 Notice of Allowance dated Nov. 15, 2018.
U.S. Appl. No. 15/354,940 Non-Final Office Action dated Nov. 2, 2018.
U.S. Appl. No. 15/593,129 Office Action dated Jan. 3, 2019.
U.S. Appl. No. 12/535,676 Office Action dated Jun. 26, 2019.
U.S. Appl. No. 13/002,136 Office Action dated Jun. 21, 2019.
U.S. Appl. No. 12/786,739 Office Action dated May 8, 2019.
U.S. Appl. No. 13/733,873 Office Action dated May 16, 2019.
U.S. Appl. No. 15/074,115 Office Action dated Mar. 6, 2019.
U.S. Appl. No. 15/089,842 Notice of Allowance dated Mar. 29, 2019.
U.S. Appl. No. 15/265,415 Notice of Allowance dated Dec. 26, 2018.
U.S. Appl. No. 15/593,121 Notice of Allowance dated Dec. 26, 2018.

Keeley et al., Gradual vs. abrupt withdrawal of methylphenidate in two older dependent males. Journal of Substance Abuse Treatment. 2(2):123-125 (1985).

Lockner et al. Dietary intake and parents' perception of mealtime behaviors in preschool-age children with autism spectrum disorder and in typically developing children. J Am Diet Assoc 108(8):1360-1363 (2008).

Naver.com entry for Rare Disease Information: Osteopenia—Osteopsathyrosis, Fragilitasossium, Fragilitasossium (accessed Sep. 25, 2019).

Singh et al. Past, Present, and Future Technologies for Oral Delivery of Therapeutic Proteins. J Pham Sci 97(7):2497-2523 (2008).

U.S. Appl. No. 16/103,192 Office Action dated Nov. 4, 2019.
U.S. Appl. No. 15/354,940 Final Office Action dated Aug. 21, 2019.

National Institutes of Health. Thin Bones Seen in Boys with Autism and Autism Spectrum Disorder. 3 pages (2008).

U.S. Appl. No. 13/733,873 Final Office Action dated Feb. 6, 2020.
U.S. Appl. No. 15/889,917 Final Office Action dated Feb. 13, 2020.
U.S. Appl. No. 15/074,115 Notice of Allowance dated Feb. 11, 2020.
U.S. Appl. No. 16/296,546 Non-Final Office Action dated Feb. 14, 2020.

Wang et al., Extraction of Pancreatin from Pig Pancreas and Isolation and Purification of Kallikrein. Academic Journal of Kunming Medical College 1: 107-108 (2002).

International Preliminary Report on Patentability dated Oct. 15, 2019 for PCT/US2018/026841.

U.S. Appl. No. 16/499,988, filed Oct. 1, 2019.
U.S. Appl. No. 15/074,115 Notice of Allowance dated Dec. 11, 2019.
U.S. Appl. No. 15/889,917 Office Action dated May 24, 2019.

European Patent Application No. EP19193479.3 Extended Search Report dated Mar. 31, 2020.

U.S. Appl. No. 12/535,676 Notice of Allowance dated Apr. 1, 2020.
U.S. Appl. No. 13/757,412 Non-Final Office Action dated Mar. 18, 2020.
U.S. Appl. No. 14/713,242 Notice of Allowance dated Apr. 2, 2020.
U.S. Appl. No. 16/422,079 Non-Final Office Action dated Apr. 20, 2020.

Nagamoto. Jacobson: Psychiatric Secrets, 2nd ed. 2001. Ch 28 Antipsychotic meds.

Neuer, et al. The role of heat shock proteins in reproduction. Hum Reprod Update. Mar.-Apr. 2008;6(2):149-59.

Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.

Newhorizons. ADD/ADHD: New Perspectives on Attentional Priority Disorders. New Horizons for Learning. Jul. 15, 2008.

NIH. National Institutes of Health. National Diabetes Statistics 2007. diabetes.niddk.nih.gov. Jun. 1, 2008.

NINDS Dysautonimia Information Page retrieved from the internet Sep. 10, 2009, http://www.ninds.nih.gov/disorders/dysautonomia/dysautonomia.htm.

Ninds Guillain-Barre Syndrome Information Page, retrieved from the internet Sep. 15, 2009, http://www.ninds.nih.gov/disorders/gbs/gbs.htm.

\* cited by examiner

METHODS AND COMPOSITIONS FOR THE PREVENTION AND TREATMENT OF INFLUENZA

CROSS-REFERENCE TO RELATED APPLICATION

This application is a continuation of U.S. application Ser. No. 13/502,989, filed Jun. 28, 2012, now U.S. Pat. No. 9,511,125, which is a § 371 U.S. National Phase Entry of PCT/US2010/053484, filed Oct. 21, 2010, which claims the benefit of U.S. Provisional Application No. 61/253,805, filed Oct. 21, 2009, incorporated by reference in its entirety herein.

TECHNICAL FIELD

This disclosure relates to the prevention and treatment of Influenza, including Influenza A Virus Subtype H1N1, with the use of a pharmaceutical composition comprising one or more digestive enzymes. The disclosure further relates to the use of an individual's fecal chymotrypsin level as an indicator, e.g., biomarker, of whether an individual may be immune-compromised and/or whether an individual may be susceptible to Influenza in general, and in particular to Influenza A Subtype H1N1, and/or as a biomarker of whether an individual will benefit from administration of a described pharmaceutical composition. This disclosure also relates to the use of compositions comprising one or more digestive enzymes as antiseptics, detergents, sanitizers, and disinfectants, e.g., as viricidal and/or viristatic compositions, to treat surfaces and thus to prevent and/or reduce the spread of Influenza infections.

BACKGROUND

Digestive enzymes are enzymes that can break down one or more components of foods, e.g., carbohydrates, lipids/fats, proteins, cellulose, nucleic acids, etc., and thereby assist in digestion and uptake of nutrients. Certain digestive enzymes are produced by the salivary glands, glands in the stomach, the pancreas, and glands in the small intestines. For example, digestive enzymes produced by the pancreas and secreted into the stomach and small intestine aid in digestion. Other digestive enzymes are produced by plants, fungi, or microorganisms (e.g., papain, bromelain).

Digestive enzymes have been administered to mammals to treat enzyme deficiencies caused by conditions affecting the pancreas, such as pancreatitis and pancreatic enzyme deficiency. Pancreatic enzymes administered to humans are commonly of porcine origin. Manufacturers of enzyme preparations have also used enteric coatings for lipase compositions in individuals with cystic fibrosis who require administration of lipases. The preparations for lipase delivery have used enteric coatings containing, for example, hypromellose phthalate, dimethicone 1000, and dibutyl phthalate.

Certain methods for coating sensitive bioactive substances such as enzymes have been described, see, e.g., U.S. Pat. No. RE40,059; 6,835,397; 6,797,291; 6,616,954; 6,312,741; 6,251,478; 6,153,236; 6,013,286, and 5,190,775, and Ser. No. 12/386,051, all of which are incorporated by reference in their entirety herein.

Influenza A (H1N1) virus is a subtype of influenza virus A and the most common cause of influenza (flu) in humans. Some strains of H1N1 are endemic in humans and cause a small fraction of all influenza-like illness and a large fraction of all seasonal influenza. H1N1 strains caused roughly half of all human flu infections in 2006. Other strains of H1N1 are endemic in pigs (swine influenza) and in birds (avian influenza).

In June 2009, WHO declared that flu due to a new strain of swine-origin H1N1 was responsible for the 2009 flu pandemic. This strain is commonly called "swine flu" by the public media.

Influenza A virus strains are categorized according to two proteins found on the surface of the virus: hemagglutinin (H) and neuraminidase (N). All influenza A viruses contain hemagglutinin and neuraminidase, but the structure of these proteins differ from strain to strain due to rapid genetic mutation in the viral genome. Influenza A virus strains are assigned an H number and an N number based on which forms of these two proteins the strain contains. There are 16 H and 9 N subtypes known in birds, but only H 1, 2 and 3, and N 1 and 2 are commonly found in humans.

The Spanish flu, also known as La Gripe Española, or La Pesadilla, was an unusually severe and deadly strain of avian influenza, a viral infectious disease, that killed some 50 million to 100 million people worldwide over about a year in 1918 and 1919. It is thought to be one of the most deadly pandemics in human history. Tt was caused by the H1N1 type of influenza virus. It is postulated that the Spanish flu caused an unusual number of deaths because it may have caused a cytokine storm in the body. The recent epidemic of bird flu, also an Influenza A virus, had a similar effect. The Spanish flu virus infected lung cells, leading to overstimulation of the immune system via release of cytokines into the lung tissue. This leads to extensive leukocyte migration towards the lungs, causing destruction of lung tissue and secretion of liquid into the organ, making it difficult for the patient to breathe. In contrast to other pandemics, which mostly kill the old and the very young, the 1918 pandemic killed unusual numbers of young adults, which may have been due to their healthy immune systems being able to mount a very strong and damaging response to the infection.

The more recent Russian flu was a 1977-1978 flu epidemic caused by strain Influenza A/USSR/90/77 (H1N1). It infected mostly children and young adults under 23 because a similar strain was prevalent in 1947-57, causing most adults to have substantial immunity. Some have called it a flu pandemic, but because it only affected the young it is not considered a true pandemic. The virus was included in the 1978-1979 influenza vaccine.

In the 2009 flu pandemic, the virus isolated from patients in the United States was found to be made up of genetic elements from four different flu viruses—North American Mexican influenza, North American avian influenza, human influenza, and swine influenza virus typically found in Asia and Europe. This strain appears to be a result of reassortment of human influenza and swine influenza viruses, in all four different strains of subtype H1N1.

Preliminary genetic characterization found that the hemagglutinin (HA) gene was similar to that of swine flu viruses present in U.S. pigs since 1999, but the neuraminidase (NA) and matrix protein (M) genes resembled versions present in European swine flu isolates. The six genes from American swine flu are themselves mixtures of swine flu, bird flu, and human flu viruses. While viruses with this genetic makeup had not previously been found to be circulating in humans or pigs, there is no formal national surveillance system to determine what viruses are circulating in pigs in the U.S.

On Jun. 11, 2009, the WHO declared an H1N1 pandemic, moving the alert level to phase 6, marking the first global pandemic since 1968.

Communicable diseases are currently the leading cause of preventable deaths worldwide, disproportionately affecting resource-poor settings. Pandemic influenzas add to already unacceptable levels of morbidity and mortality from diarrhea, malaria, pneumonia, malnutrition, HIV/AIDS and tuberculosis, in addition to causing high maternal and neonatal death rates. A few key conditions cause 90% of deaths from communicable diseases: pneumonia (3.9 million deaths per year); diarrhoeal diseases (1.8 million); and malaria (1.2 million). Malnutrition is a significant contributing factor to this mortality. During a pandemic, these illnesses are likely to increase in resource-poor settings where chronically strained health systems would face even higher patient volumes, severe resource constraints, and absenteeism of critical staff.

The current prophylactic means for preventing the flu is by Injectable Inactivated Vaccine or Nasal Spray Flu Vaccine. Commonly called the "flu shot", the Injectable Inactivated Vaccine method employs an inactivated vaccine (containing killed virus) that is given with a needle, usually in the arm. The flu shot is approved for use in people older than 6 months, including healthy people and people with chronic medical conditions. Alternately, the nasal-spray flu vaccine—a vaccine made with live, weakened flu viruses that do not cause the flu (sometimes called LAIV for "live attenuated influenza vaccine" or FluMist®). LAIV (FluMist®) is approved for use in healthy people 2-49 years of age who are not pregnant.

Typically each vaccine contains three influenza viruses-one A (H3N2) virus, one A (H1N1) virus, and one B virus. The viruses in the vaccine change each year based on international surveillance and scientists' estimations about which types and strains of viruses will circulate in a given year. About 2 weeks after vaccination, antibodies that provide protection against influenza virus infection develop in the body.

Annual influenza vaccination is the most effective method for preventing influenza virus infection and its complications. Influenza vaccine can be administered to any person aged >6 months (who does not have contraindications to vaccination) to reduce the likelihood of becoming ill with influenza or of transmitting influenza to others. Trivalent inactivated influenza vaccine (TIV) can be used for any person aged >6 months, including those with high-risk conditions. Live, attenuated influenza vaccine (LAW) may be used for healthy, nonpregnant persons aged 2-49 years. If vaccine supply is limited, priority for vaccination is typically assigned to persons in specific groups and of specific ages who are, or are contacts of, persons at higher risk for influenza complications. Because the safety or effectiveness of LAIV has not been established in persons with underlying medical conditions that confer a higher risk for influenza complications, these persons should only be vaccinated with TIV. Influenza viruses undergo frequent antigenic change (i.e., antigenic drift), and persons recommended for vaccination must receive an annual vaccination against the influenza viruses forecasted to be in circulation. Although vaccination coverage has increased in recent years for many groups targeted for routine vaccination, coverage remains low among most of these groups.

Antiviral medications are an adjunct to vaccination and are effective when administered as treatment and when used for chemoprophylaxis after an exposure to influenza virus. Oseltamivir and zanamivir are the only antiviral medications recommended for use in the United States. Amantadine or rimantidine should not be used for the treatment or prevention of influenza in the United States until evidence of susceptibility to these antiviral medications has been reestablished among circulating influenza A viruses.

The efficacy (i.e., prevention of illness among vaccinated persons in controlled trials) and effectiveness (i.e., prevention of illness in vaccinated populations) of influenza vaccines depend in part on the age and immunocompetence of the vaccine recipient, the degree of similarity between the viruses in the vaccine and those in circulation, and the outcome being measured. Influenza vaccine efficacy and effectiveness studies have used multiple possible outcome measures, including the prevention of medically attended acute respiratory illness (MAARI), prevention of laboratory-confirmed influenza virus illness, prevention of influenza or pneumonia-associated hospitalizations or deaths, or prevention of seroconversion to circulating influenza virus strains.

Efficacy or effectiveness for more specific outcomes such as laboratory-confirmed influenza typically will be higher than for less specific outcomes such as MAARI because the causes of MAARI include infections with other pathogens that influenza vaccination would not be expected to prevent. Observational studies that compare less-specific outcomes among vaccinated populations to those among unvaccinated populations are subject to biases that are difficult to control for during analyses. For example, an observational study that determines that influenza vaccination reduces overall mortality might be biased if healthier persons in the study are more likely to be vaccinated. Randomized controlled trials that measure laboratory-confirmed influenza virus infections as the outcome are the most persuasive evidence of vaccine efficacy, but such trials cannot be conducted ethically among groups recommended to receive vaccine annually.

Both LAIV and TIV contain strains of influenza viruses that are antigenically equivalent to the annually recommended strains: one influenza A (H3N2) virus, one influenza A (H1N1) virus, and one influenza B virus. Each year, one or more virus strains in the vaccine might be changed on the basis of global surveillance for influenza viruses and the emergence and spread of new strains. All three vaccine virus strains were changed for the recommended vaccine for the 2008-09 influenza season, compared with the 2007-08 season.

During the preparation of TIV, the vaccine viruses are made noninfectious (i.e., inactivated or killed). Only subvirion and purified surface antigen preparations of TIV (often referred to as "split" and subunit vaccines, respectively) are available in the United States. TIV contains killed viruses and thus cannot cause influenza. LAIV contains live, attenuated viruses that have the potential to cause mild signs or symptoms such as runny nose, nasal congestion, fever or sore throat. LAIV is administered intranasally by sprayer, whereas TIV is administered intramuscularly by injection. LAW is licensed for use among nonpregnant persons aged 2-49 years; safety has not been established in persons with underlying medical conditions that confer a higher risk of influenza complications. TIV is licensed for use among persons aged >6 months, including those who are healthy and those with chronic medical conditions. LAW is generally regarded as more efficacious and effective than TIV.

In many populations, there remains a need for alternatives to TIV and LAW, and a need for adjunctive prophylactic or therapeutic regimens for the prevention and/or treatment of Influenza.

Pregnant Women and Neonates—

Pregnant women have protective levels of anti-influenza antibodies after vaccination. Passive transfer of anti-influenza antibodies that might provide protection from vaccinated women to neonates has been reported. A retrospective, clinic-based study conducted during 1998-2003 documented a non-significant trend towards fewer episodes of MAARI during one influenza season among vaccinated pregnant women compared with unvaccinated pregnant women and substantially fewer episodes of MAARI during the peak influenza season. However, a retrospective study conducted during 1997-2002 that used clinical records data did not indicate a reduction in ILI among vaccinated pregnant women or their infants. In another study conducted during 1995-2001, medical visits for respiratory illness among the infants were not substantially reduced. However, studies of influenza vaccine effectiveness among pregnant women have not included specific outcomes such as laboratory-confirmed influenza in women or their infants.

Elderly Population—

Adults aged >65 years typically have a diminished immune response to influenza vaccination compared with young healthy adults, suggesting that immunity might be of shorter duration (although still extending through one influenza season). However, a review of the published literature concluded that no clear evidence existed that immunity declined more rapidly in the elderly. Infections among the vaccinated elderly might be associated with an age-related reduction in ability to respond to vaccination rather than reduced duration of immunity. The only randomized controlled trial among community-dwelling persons aged >60 years reported a vaccine efficacy of 58% against influenza respiratory illness during a season when the vaccine strains were considered to be well-matched to circulating strains, but indicated that efficacy was lower among those aged >70 years. Influenza vaccine effectiveness in preventing MAARI among the elderly in nursing homes has been estimated at 20%-40%, and reported outbreaks among well-vaccinated nursing home populations have suggested that vaccination might not have any significant effectiveness when circulating strains are drifted from vaccine strains. In contrast, some studies have indicated that vaccination can be up to 80% effective in preventing influenza-related death. Among elderly persons not living in nursing homes or similar chronic-care facilities, influenza vaccine is 27%-70% effective in preventing hospitalization for pneumonia and influenza. Influenza vaccination reduces the frequency of secondary complications and reduces the risk for influenza-related hospitalization and death among community-dwelling adults aged >65 years with and without high-risk medical conditions (e.g., heart disease and diabetes). However, studies demonstrating large reductions in hospitalizations and deaths among the vaccinated elderly have been conducted using medical record databases and have not measured reductions in laboratory-confirmed influenza illness. These studies have been challenged because of concerns that they have not adequately controlled for differences in the propensity for healthier persons to be more likely than less healthy persons to receive vaccination.

HIV Compromised Individuals—

TIV produces adequate antibody concentrations against influenza among vaccinated HIV-infected persons who have minimal AIDS-related symptoms and normal or near-normal CD4+ T-lymphocyte cell counts. Among persons who have advanced HIV disease and low CD4+ T-lymphocyte cell counts, TIV might not induce protective antibody titers; a second dose of vaccine does not improve the immune response in these persons. A randomized, placebo-controlled trial determined that TIV was highly effective in preventing symptomatic, laboratory-confirmed influenza virus infection among HIV-infected persons with a mean of 400 CD4+ T-lymphocyte cells/mm3; however, a limited number of persons with CD4+ T-lymphocyte cell counts of <200 were included in that study. A nonrandomized study of HIV-infected persons determined that influenza vaccination was most effective among persons with >100 CD4+ cells and among those with <30,000 viral copies of HIV type-1/mL.

Transplant Recipients—

On the basis of certain small studies, immunogenicity for persons with solid organ transplants varies according to transplant type. Among persons with kidney or heart transplants, the proportion that developed seroprotective antibody concentrations was similar or slightly reduced compared with healthy persons. However, a study among persons with liver transplants indicated reduced immunologic responses to influenza vaccination, especially if vaccination occurred within the 4 months after the transplant procedure.

Other Medical Conditions— persons with underlying medical conditions including asthma, reactive airways disease, or other chronic disorders of the pulmonary or cardiovascular systems; metabolic diseases such as diabetes, renal dysfunction, and hemoglobinopathies; or known or suspected immunodeficiency diseases or immunosuppressed states should not be vaccinated with LAIV. In addition children or adolescents receiving aspirin or other salicylates should not be vaccinated with a LAIV because of the association of Reye syndrome and salicylates with wild-type influenza virus infection. Individuals with acute febrile illness should not be vaccinated with TIV or LAIV.

Pediatric Chronic Medical Conditions—

Among children with high-risk medical conditions, one study of 52 children aged 6 months-3 years reported fever among 27% and irritability and insomnia among 25% (113); and a study among 33 children aged 6-18 months reported that one child had irritability and one had a fever and seizure after vaccination. No placebo comparison group was used in these studies.

Hypersensitivity and Allergic Reactions—

Immediate and presumably allergic reactions (e.g., hives, angioedema, allergic asthma, and systemic anaphylaxis) occur rarely after influenza vaccination. These reactions probably result from hypersensitivity to certain vaccine components; the majority of reactions probably are caused by residual egg protein. Although influenza vaccines contain only a limited quantity of egg protein, this protein can induce immediate hypersensitivity reactions among persons who have severe egg allergy. Manufacturers use a variety of different compounds to inactivate influenza viruses and add antibiotics to prevent bacterial contamination. Persons who have experienced hives or swelling of the lips or tongue, or who have experienced acute respiratory distress or who collapse after eating eggs, must consult a physician for appropriate evaluation to help determine if vaccine should be administered. Persons who have documented immunoglobulin E (IgE)-mediated hypersensitivity to eggs, including those who have had occupational asthma related to egg exposure or other allergic responses to egg protein, also might be at increased risk for allergic reactions to influenza vaccine, and consultation with a physician before vaccination must be considered. Hypersensitivity reactions to other vaccine components can occur but are rare. Although exposure to vaccines containing thimerosal can lead to hypersensitivity, the majority of patients do not have reactions to thimerosal when it is administered as a component of vaccines, even when patch or intradermal tests for thimerosal indicate hypersensitivity. When reported, hypersensitivity to thimerosal typically has consisted of local delayed hypersensitivity reactions.

Guillain-Barré Syndrome—

The annual incidence of Guillain-Barré Syndrome (GBS) is 10-20 cases per 1 million adults. Substantial evidence exists that multiple infectious illnesses, most notably *Campylobacter jejuni* gastrointestinal infections and upper respiratory tract infections, are associated with GBS. The 1976 swine influenza vaccine was associated with an increased frequency of GBS, estimated at one additional case of GBS per 100,000 persons vaccinated. The risk for influenza vaccine-associated GBS was higher among persons aged >25 years than among persons aged <25 years. However, obtaining strong epidemiologic evidence for a possible small increase in risk for a rare condition with multiple causes is difficult, and no evidence exists for a consistent causal relation between subsequent vaccines prepared from other influenza viruses and GBS.

None of the studies conducted using influenza vaccines other than the 1976 swine influenza vaccine have demonstrated a substantial increase in GBS associated with influenza vaccines. During three of four influenza seasons studied during 1977-1991, the overall relative risk estimates for GBS after influenza vaccination were not statistically significant in any of these studies. However, in a study of the 1992-93 and 1993-94 seasons, the overall relative risk for GBS was 1.7 (CI=1.0-2.8; p=0.04) during the 6 weeks after vaccination, representing approximately one additional case of GBS per 1 million persons vaccinated; the combined number of GBS cases peaked 2 weeks after vaccination. Results of a study that examined health-care data from Ontario, Canada, during 1992-2004 demonstrated a small but statistically significant temporal association between receiving influenza vaccination and subsequent hospital admission for GBS. However, no increase in cases of GBS at the population level was reported after introduction of a mass public influenza vaccination program in Ontario beginning in 2000. Data from VAERS have documented decreased reporting of GBS occurring after vaccination across age groups over time, despite overall increased reporting of other, non-GBS conditions occurring after administration of influenza vaccine. Cases of GBS after influenza virus infection have been reported, but no other epidemiologic studies have documented such an association. Recently published data from the United Kingdom's General Practice Research Database (GPRD) found influenza vaccine to be protective against GBS, although it is unclear if this was associated with protection against influenza or confounding because of a "healthy vaccine" (e.g., healthier persons might be more likely to be vaccinated and are lower risk for GBS). A separate GPRD analysis found no association between vaccination and GBS over a 9 year period; only three cases of GBS occurred within 6 weeks after influenza vaccine.

It is not known if GBS is a side effect of influenza vaccines other than 1976 swine influenza vaccine; the estimated risk for GBS (on the basis of the few studies that have demonstrated an association between vaccination and GBS) is low (i.e., approximately one additional case per 1 million persons vaccinated). It has been deemed by the CDC and others that the potential benefits of influenza vaccination in preventing serious illness, hospitalization, and death substantially outweigh these estimates of risk for vaccine-associated GBS. No evidence indicates that the case fatality ratio for GBS differs among vaccinated persons and those not vaccinated The incidence of GBS among the general population is low, but persons with a history of GBS have a substantially greater likelihood of subsequently experiencing GBS when injected with TIV influenza vaccine than persons without such a history. Thus, the likelihood of coincidentally experiencing GBS after influenza vaccination is expected to be greater among persons with a history of GBS than among persons with no history of this syndrome. Whether influenza vaccination specifically might increase the risk for recurrence of GBS is unknown. However, avoiding vaccinating persons who are not at high risk for severe influenza complications and who are known to have experienced GBS within 6 weeks after a previous influenza vaccination is often taken as a prudent as a precaution. As an alternative, physicians use influenza antiviral chemoprophylaxis for these persons. Although data are limited, the established benefits of influenza vaccination might outweigh the risks for many persons who have a history of GBS and who are also at high risk for severe complications from influenza.

Viral Shedding—

Available data indicates that both children and adults vaccinated with LAIV can shed vaccine viruses after vaccination, although in lower amounts than occur typically with shedding of wild-type influenza viruses. In rare instances, shed vaccine viruses can be transmitted from vaccine recipients to unvaccinated persons. However, serious illnesses have not been reported among unvaccinated persons who have been infected inadvertently with vaccine viruses.

One study of children aged 8-36 months in a child care center assessed transmissibility of vaccine viruses from 98 vaccinated to 99 unvaccinated subjects; 80% of vaccine recipients shed one or more virus strains (mean duration: 7.6 days). One influenza type B vaccine strain isolate was recovered from a placebo recipient and was confirmed to be vaccine-type virus. The type B isolate retained the cold-adapted, temperature-sensitive, attenuated phenotype, and it possessed the same genetic sequence as a virus shed from a vaccine recipient who was in the same play group. The placebo recipient from whom the influenza type B vaccine strain was isolated had symptoms of a mild upper respiratory illness but did not experience any serious clinical events. The estimated probability of acquiring vaccine virus after close contact with a single LAIV recipient in this child care population was 0.6%-2.4%.

Studies assessing whether vaccine viruses are shed have been based on viral cultures or PCR detection of vaccine viruses in nasal aspirates from persons who have received LAIV. One study of 20 healthy vaccinated adults aged 18-49 years demonstrated that the majority of shedding occurred within the first 3 days after vaccination, although the vaccine virus was detected in one subject on day 7 after vaccine receipt. Duration or type of symptoms associated with receipt of LAIV did not correlate with detection of vaccine viruses in nasal aspirates. Another study in 14 healthy adults aged 18-49 years indicated that 50% of these adults had viral antigen detected by direct immunofluorescence or rapid antigen tests within 7 days of vaccination. The majority of samples with detectable virus were collected on day 2 or 3. Vaccine strain virus was detected from nasal secretions in one (2%) of 57 HIV-infected adults who received LAIV, none of 54 HIV-negative participants (256), and three (13%) of 23 HIV-infected children compared with seven (28%) of 25 children who were not HIV-infected. No participants in these studies had detectable virus beyond 10 days after receipt of LAIV. The possibility of person-to-person transmission of vaccine viruses was not assessed in these studies.

LAIV Side Effects—

In a subset of healthy children aged 60-71 months from one clinical trial (233), certain signs and symptoms were reported more often after the first dose among LAIV recipients (n=214) than among placebo recipients (n=95), including runny nose (48% and 44%, respectively); headache (18% and 12%, respectively); vomiting (5% and 3%, respectively); and myalgias (6% and 4%, respectively). However, these differences were not statistically significant. In other trials, signs and symptoms reported after LAIV administration have included runny nose or nasal congestion (20%-75%), headache (2%-46%), fever (0-26%), vomiting (3%-13%), abdominal pain (2%), and myalgias (0-21%). These symptoms were associated more often with the first dose and were self-limited.

In a randomized trial published in 2007, LAIV and TIV were compared among children aged 6-59 months. Children with medically diagnosed or treated wheezing within 42 days before enrollment, or a history of severe asthma, were excluded from this study. Among children aged 24-59 months who received LAIV, the rate of medically significant wheezing, using a pre-specified definition, was not greater compared with those who received TIV; wheezing was observed more frequently among younger LAW recipients in this study. In a previous randomized placebo-controlled safety trial among children aged 12 months-17 years without a history of asthma by parental report, an elevated risk for asthma events (RR=4.06, CI=1.29-17.86) was documented among 728 children aged 18-35 months who received LAIV. Of the 16 children with asthma-related events in this study, seven had a history of asthma on the basis of subsequent medical record review. None required hospitalization, and elevated risks for asthma were not observed in other age groups.

Among adults aged 19-49, runny nose or nasal congestion (28%-78%), headache (16%-44%), and sore throat (15%-27%) have been reported more often among vaccine recipients than placebo recipients. In one clinical trial among a subset of healthy adults aged 18-49 years, signs and symptoms reported more frequently among LAW recipients (n=2,548) than placebo recipients (n=1,290) within 7 days after each dose included cough (14% and 11%, respectively); runny nose (45% and 27%, respectively); sore throat (28% and 17%, respectively); chills (9% and 6%, respectively); and tiredness/weakness (26% and 22%, respectively).

There are additional reasons why it would be useful to have alternative or adjunctive prophylactic and/or therapeutic options for the prevention and/or treatment of Influenza, as discussed below.

Challenging Prediction of Virus Strains—

Manufacturing trivalent influenza virus vaccines is a challenging process that takes 6-8 months to complete. This manufacturing timeframe requires that influenza vaccine strains for influenza vaccines used in the United States must be selected in February of each year by the FDA to allow time for manufacturers to prepare vaccines for the next influenza season. Vaccine strain selections are based on global viral surveillance data that is used to identify trends in antigenic changes among circulating influenza viruses and the availability of suitable vaccine virus candidates.

Vaccination can provide reduced but substantial cross-protection against drifted strains in some seasons, including reductions in severe outcomes such as hospitalization. Usually one or more circulating viruses with antigenic changes compared with the vaccine strains are identified in each influenza season. However, assessment of the clinical effectiveness of influenza vaccines cannot be determined solely by laboratory evaluation of the degree of antigenic match between vaccine and circulating strains. In some influenza seasons, circulating influenza viruses with significant antigenic differences predominate and, compared with seasons when vaccine and circulating strains are well-matched, reductions in vaccine effectiveness are sometimes observed. However, even during years when vaccine strains were not antigenically well matched to circulating strains, substantial protection has been observed against severe outcomes, presumably because of vaccine-induced cross-reacting antibodies. For example, in one study conducted during an influenza season (2003-04) when the predominant circulating strain was an influenza A (H3N2) virus that was antigenically different from that season's vaccine strain, effectiveness among persons aged 50-64 years against laboratory-confirmed influenza illness was 60% among healthy persons and 48% among persons with medical conditions that increase risk for influenza complications. An interim, within-season analysis during the 2007-08 influenza season indicated that vaccine effectiveness was 44% overall, 54% among healthy persons aged 5-49 years, and 58% against influenza A, despite the finding that viruses circulating in the study area were predominately a drifted influenza A H3N2 and a influenza B strain from a different lineage compared with vaccine strains. Among children, both TIV and LAW provide protection against infection even in seasons when vaccines and circulating strains are not well matched. Vaccine effectiveness against ILI was 49%-69% in two observational studies, and 49% against medically attended, laboratory-confirmed influenza in a case-control study conducted among young children during the 2003-04 influenza season, when a drifted influenza A H3N2 strain predominated, based on viral surveillance data. However, the FDA admits that continued improvements in collecting representative circulating viruses and use surveillance data to forecast antigenic drift are needed. Shortening manufacturing time to increase the time to identify good vaccine candidate strains from among the most recent circulating strains also is also important. Data from multiple seasons and collected in a consistent manner are needed to better understand vaccine effectiveness during seasons when circulating and vaccine virus strains are not well-matched.

Vaccine Coverage— vaccination coverage of the population is influenced by a multitude of factors including vaccine supply delays and shortages, changes in influenza vaccination recommendations and target groups for vaccination, reimbursement rates for vaccine and vaccine administration, and other factors related to vaccination coverage among adults and children. Production issues coupled with the requirement to forecast appropriate influenza types and antigens have caused severe shortfalls in vaccine availability, for example in the years 2004-05 an American company, Chiron, had their operating license suspended by British officials following problems at their manufacturing plant in Liverpool, England. Due to contamination in a batch of vaccines intended for American market they were unable to supply their flu vaccine, Fluvirin. Fluvirin made up approximately 50% of America's expected demand for the winter flu season.

Because of the inherent risk factors and the reluctance of individuals to accept those risks, many at risk groups have very low vaccination coverage. For example vaccine coverage among pregnant women has not increased significantly during the preceding decade. Only 12% and 13% of pregnant women participating in the 2006 and 2007 NHIS reported vaccination during the 2005-06 and 2006-07 seasons, respectively, excluding pregnant women who reported diabetes, heart disease, lung disease, and other selected high-risk conditions. In a study of influenza vaccine acceptance by pregnant women, 71% of those who were offered the vaccine chose to be vaccinated. However, a 1999 survey of obstetricians and gynecologists determined that only 39% administered influenza vaccine to obstetric patients in their practices, although 86% agreed that pregnant women's risk for influenza-related morbidity and mortality increases during the last two trimesters.

Drug Resistance—

Viral neuraminidase is an enzyme on the surface of influenza viruses that enables the virus to be released from the host cell. Drugs that inhibit neuraminidase are often used to treat influenza. Neuraminidase has been targeted in structure-based enzyme inhibitor design programmes that have resulted in the production of two drugs, zanamivir (Relenza) and oseltamivir (Tamiflu). Administration of neuraminidase inhibitors is a treatment that limits the severity and spread of viral infections. Neuraminidase inhibitors are useful for combating influenza infection: zanamivir, administered by inhalation; oseltamivir, administered orally; and under research is peramivir administered parenterally, that is through intravenous or intramuscular injection.

On Feb. 27, 2005, a 14-year-old Vietnamese girl was documented to be carrying an H5N1 influenza virus strain that was resistant to the drug oseltamivir. The drug is used to treat patients that have contracted influenza. However, the Vietnamese girl who had received a prophylaxis dose (75 mg once a day) was found to be non-responsive to the medication. In growing fears of a global avian flu pandemic, scientists began to look for a cause of resistance to the Tamiflu medication. The cause was determined to be a histidine-to-tryosine (amino acid) substitution at position 274 in its neuraminidase protein.

SUMMARY

This disclosure relates to the prevention and/or treatment of Influenza, including Influenza A Virus Subtype H1N1, with the use of a pharmaceutical composition comprising one or more digestive enzymes, including pancreatic or other digestive-track enzymes (e.g., porcine pancreatic enzymes or bird-derived digestive track enzymes) or plant-, fungal-, or microorganism-derived enzymes, that break down components of food. As used herein, a pharmaceutical composition can be used for human or veterinary indications. Accordingly, the pharmaceutical compositions can be useful for prophylactic and/or therapeutic treatment of human or other mammalian populations (e.g., pig, horse, cow, sheep, goat, monkey, rat, mouse, cat, dog) or of bird populations (e.g., duck, goose, chicken, turkey). The disclosure further relates to the use of an individual's (e.g., a human's) fecal chymotrypsin level as an indicator, e.g., biomarker, of whether an individual may be immune-compromised and/or whether an individual may be susceptible to Influenza in general, and in particular to Influenza A Subtype H1N1, and/or as a biomarker of whether an individual will benefit from administration of a described pharmaceutical composition, e.g., to prevent and/or treat Influenza. The compositions can be used on their own, and/or as adjuncts to vaccination or other anti-viral regimens, and/or with other therapeutic or anti-viral agents post-infection to treat Influenza.

The present disclosure also relates to enzyme delivery systems comprising digestive enzyme preparations, which are useful in the prophylaxis and treatment of influenza in general and more particularly useful for the prevention and treatment of Influenza A Virus, Subtype H1N1, including H1N1 variants swine influenza (endemic in pigs) and avian influenza (endemic in birds). In some embodiments, the digestive enzyme preparations of this disclosure permit controlled delivery of enzymes having increased stability and enhanced administration properties for the prevention of influenza infection and treatment of influenza symptoms.

In virus classification the influenza virus is an RNA virus of three of the five genera of the family Orthomyxoviridae: Influenzavirus A, Influenzavirus B, Influenzavirus C. These viruses are only distantly related to the human parainfluenza viruses, which are RNA viruses belonging to the paramyxovirus family that are a common cause of respiratory infections in children such as croup, but can also cause a disease similar to influenza in adults.

Influenza viruses A, B and C are very similar in overall structure. The virus particle is 80-120 nanometres in diameter and usually roughly spherical, although filamentous forms can occur. These filamentous forms are more common in influenza C, which can form cordlike structures up to 500 micrometres long on the surfaces of infected cells. However, despite these varied shapes, the viral particles of all influenza viruses are similar in composition. These are made of a viral envelope containing two main types of glycoproteins, wrapped around a central core. The central core contains the viral RNA genome and other viral proteins that package and protect this RNA. Unusually for a virus, its genome is not a single piece of nucleic acid; instead, it contains seven or eight pieces of segmented negative-sense RNA, each piece of RNA contains either one or two genes. For example, the influenza A genome contains 11 genes on eight pieces of RNA, encoding for 11 proteins: hemagglutinin (HA), neuraminidase (NA), nucleoprotein (NP), M1, M2, NS1, NS2(NEP), PA, PB1, PB1-F2 and PB2.

Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to HA and NA. These different types of HA and NA form the basis of the H and N distinctions in, for example, H5N1. There are 16 H and 9 N subtypes known, but only H 1, 2 and 3, and N 1 and 2 are commonly found in humans.

There are at least 16 different HA antigens. These subtypes are labeled H1 through H16. The last, H16, was discovered only recently on influenza A viruses isolated from black-headed gulls from Sweden and Norway. The first three hemagglutinins, H1, H2, and H3, are found in human influenza viruses.

A highly pathogenic avian flu virus of H5N1 type has been found to infect humans at a low rate. It has been reported that single amino acid changes in this avian virus strain's type H5 hemagglutinin have been found in human patients that "can significantly alter receptor specificity of avian H5N1 viruses, providing them with an ability to bind to receptors optimal for human influenza viruses". This finding seems to explain how an H5N1 virus that normally does not infect humans can mutate and become able to efficiently infect human cells. The hemagglutinin of the H5N1 virus has been associated with the high pathogenicity of this flu virus strain, apparently due to its ease of conversion to an active form by proteolysis.

HA has two primary functions: allowing the recognition of target vertebrate cells, accomplished through the binding of these cells' sialic acid-containing receptors, and allowing the entry of the viral genome into the target cells by causing the fusion of host endosomal membrane with the viral membrane.

HA binds to the monosaccharide sialic acid which is present on the surface of its target cells. This causes the viral particles to stick to the cell's surface. The cell membrane then engulfs the virus and the portion of the membrane that encloses it pinches off to form a new membrane-bound compartment within the cell called an endosome, which contains the engulfed virus. The cell then attempts to begin digesting the contents of the endosome by acidifying its interior and transforming it into a lysosome. However, as soon as the pH within the endosome drops to about 6.0, the original folded structure of the HA molecule becomes unstable, causing it to partially unfold, and releasing a very hydrophobic portion of its peptide chain that was previously hidden within the protein. This so-called "fusion peptide" acts like a molecular grappling hook by inserting itself into the endosomal membrane and locking on. Then, when the rest of the HA molecule refolds into a new structure (which is more stable at the lower pH), it "retracts the grappling hook" and pulls the endosomal membrane right up next to the virus particle's own membrane, causing the two to fuse together. Once this has happened, the contents of the virus, including its RNA genome, are free to pour out into the cell's cytoplasm.

HA is a homotrimeric integral membrane glycoprotein. It is shaped like a cylinder, and is approximately 13.5 nanometres long. The three identical monomers that constitute HA are constructed into a central a helix coil; three spherical heads contain the sialic acid binding sites. HA monomers are synthesized as precursors that are then glycosylated and cleaved into two smaller polypeptides: the HA1 and HA2 subunits. Each HA monomer consists of a long, helical chain anchored in the membrane by HA2 and topped by a large HA1 globule.

Viral neuraminidase is an enzyme on the surface of influenza viruses that enables the virus to be released from the host cell. Drugs that inhibit neuraminidase are often used to treat influenza. When influenza virus reproduces, it moves to the cell surface with a hemagglutinin molecule on the surface of the virus bound to a sialic acid receptor on the surface of the cell. In order for the virus to be released free from the cell, neuraminidase must break apart (cleave) the sialic acid receptor. In some viruses, a hemagglutinin-neuraminidase protein combines the neuraminidase and hemagglutinin functions in a single protein.

The viral neuraminidase enzyme helps viruses to be released from a host cell. Influenza virus membranes contain two glycoproteins: haemagglutinin and neuraminidase. While the hemagglutinin on the surface of the virion is needed for infection, its presence inhibits release of the particle after budding. It also mediates cell-surface sialic acid receptor binding to initiate virus infection. Viral neuraminidase cleaves terminal neuraminic acid (also called sialic acid) residues from glycan structures on the surface of the infected cell. This promotes the release of progeny viruses and the spread of the virus from the host cell to uninfected surrounding cells. Neuraminidase also cleaves sialic acid residues from viral proteins, preventing aggregation of viruses.

Ideally, influenza virus neuraminidase (NA) should act on the same type of receptor the virus hemagglutinin (HA) binds to, a phenomenon which does not always happen. It is not quite clear how the virus manages to function when there is no close match between the specificities of NA and HA.

The viral neuraminidase enzyme can have endo- or exo-glycosidase activity, and are classified as EC 3.2.1.29 (endo-neuraminidase) and EC 3.2.1.18 (exo-neuraminidases). In general, mammalian sialic acid residues are at terminal positions (non-reducing end) in complex glycans, and so viral neuraminidases which are exo-glycosidase enzymes use these terminal residues as their substrates.

Influenza viruses bind through hemagglutinin onto sialic acid sugars on the surfaces of epithelial cells; typically in the nose, throat and lungs of mammals and intestines of birds (Stage 1 in infection). After the hemagglutinin is cleaved by a protease, the cell imports the virus by endocytosis.

Once inside the cell, the acidic conditions in the endosome cause two events to happen: first part of the hemagglutinin protein fuses the viral envelope with the vacuole's membrane, then the M2 ion channel allows protons to move through the viral envelope and acidify the core of the virus, which causes the core to dissemble and release the viral RNA and core proteins. The viral RNA (vRNA) molecules, accessory proteins and RNA-dependent RNA polymerase are then released into the cytoplasm (Stage 2). The M2 ion channel is blocked by amantadine drugs, preventing infection.

These core proteins and vRNA form a complex that is transported into the cell nucleus, where the RNA-dependent RNA polymerase begins transcribing complementary positive-sense vRNA (Steps 3a and b). The vRNA is either exported into the cytoplasm and translated (step 4), or remains in the nucleus. Newly synthesized viral proteins are either secreted through the Golgi apparatus onto the cell surface (in the case of neuraminidase and hemagglutinin, step 5b) or transported back into the nucleus to bind vRNA and form new viral genome particles (step 5a). Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA polymerase, and other viral proteins are assembled into a virion. Hemagglutinin and neuraminidase molecules cluster into a bulge in the cell membrane. The vRNA and viral core proteins leave the nucleus and enter this membrane protrusion (step 6). The mature virus buds off from the cell in a sphere of host phospholipid membrane, acquiring hemagglutinin and neuraminidase with this membrane coat (step 7). As before, the viruses adhere to the cell through hemagglutinin; the mature viruses detach once their neuraminidase has cleaved sialic acid residues from the host cell. Drugs that inhibit neuraminidase, such as oseltamivir, therefore prevent the release of new infectious viruses and halt viral replication. After the release of new influenza viruses, the host cell dies.

Because of the absence of RNA proofreading enzymes, the RNA-dependent RNA polymerase that copies the viral genome makes an error roughly every 10 thousand nucleotides, which is the approximate length of the influenza vRNA. Hence, the majority of newly manufactured influenza viruses are mutants, this causes "antigenic drift", which is a slow change in the antigens on the viral surface over time. The separation of the genome into eight separate segments of vRNA allows mixing or reassortment of vRNAs if more than one type of influenza virus infects a single cell. The resulting rapid change in viral genetics produces antigenic shifts, which are sudden changes from one antigen to another. These sudden large changes allow the virus to infect new host species and quickly overcome protective immunity.

New research shows that the 2009 H1N1 "swine flu" virus may lack a piece of genetic material that has been present in all other pandemic flu viruses, meaning that this flu may not be quite as transmissible as other flu viruses. However, in two instances discovered thus far, one in Denmark and one in Japan, the virus has been found to be resistant to antiviral drugs, which is concerning as these drugs may provide some defense if taken early on in the illness.

New mutations in the H1N1 virus are believed to allow it to flourish in the small intestine, which is something that "normal" influenza cannot do. Researchers believe this is why the H1N1 virus can cause gastrointestinal symptoms, such as nausea, vomiting and diarrhea. Seasonal influenza typically causes respiratory symptoms without the gastrointestinal symptoms seen in the H1N1 virus.

Accordingly, while not bound by theory, the etiology of influenza susceptibility may be caused, in part, by an inadequate response of the human gastrointestinal immune system, e.g., in populations such as the elderly and children, and in immune-compromised individuals.

Given the above, it is a goal of the present disclosure to provide therapeutic methods and pharmaceutical compositions for the prevention and treatment of influenza by supplementing the normal pancreatic functions and functions of the gastrointestinal immune system with digestive enzyme preparations, including the pharmaceutical compositions described herein.

Another goal of the present disclosure is the use of pancreatic enzymes to provide therapeutic methods and pharmaceutical compositions for the prevention and treatment of Influenza A, Subtype H1N1 swine flu.

Another goal of the present disclosure is the use of avian proventriculus and small intestine enzymes to provide therapeutic methods and pharmaceutical compositions for the prevention of Influenza A, Subtype H1N1 avian flu.

Another goal of the present disclosure is the provision of pharmaceutical compositions for the prevention and/or treatment of the Influenza, wherein the compositions comprise one or more digestive enzymes, e.g., one or more enzymes selected from amylases, proteases, cellulases, papain (e.g., from papaya), bromelain (e.g., from pineapples), lipases, chymotrypsin, trypsin, and hydrolases. In some embodiments, the pharmaceutical compositions are lipid encapsulated.

Another goal of the present disclosure is to provide a prophylactic measure against influenza for pregnant women, neonates, and infants.

Another goal of the present disclosure is to provide a treatment for the symptoms of influenza for pregnant women, neonates, and infants.

Another goal of the present disclosure is to provide a prophylactic measure against influenza for the elderly, including those that do not respond well to vaccination.

Another goal of the present disclosure is to provide a treatment for the symptoms of influenza in the elderly.

Another goal of the present disclosure is to provide a prophylactic measure against influenza for HTV compromised individuals and those with ATDS.

Another goal of the present disclosure is to provide a treatment for the symptoms of influenza in HIV compromised individuals and those with AIDS.

Another goal of the present disclosure is to provide a prophylactic measure against influenza for organ transplant recipients.

Another goal of the present disclosure is to provide a treatment for the symptoms of influenza for organ transplant recipients.

Another goal of the present disclosure is to provide a prophylactic measure against influenza for persons with any underlying medical conditions including asthma, reactive airways disease, or other chronic disorders of the pulmonary or cardiovascular systems; other underlying medical conditions, including such metabolic diseases as diabetes, renal dysfunction, and hemoglobinopathies; or known or suspected immunodeficiency diseases or immunosuppressed states.

Another goal of the present disclosure is to provide a treatment for the symptoms of influenza for persons with underlying medical conditions including asthma, reactive airways disease, or other chronic disorders of the pulmonary or cardiovascular systems; other underlying medical conditions, including such metabolic diseases as diabetes, renal dysfunction, and hemoglobinopathies; or known or suspected immunodeficiency diseases or immunosuppressed states.

Another goal of the present disclosure is to provide a prophylactic measure against influenza for children or adolescents receiving aspirin or other salicylates due to increased risk of Reye Syndrome.

Another goal of the present disclosure is to provide a treatment for the symptoms of influenza for children or adolescents receiving aspirin or other salicylates due to increased risk of Reye Syndrome.

Another goal of the present disclosure is to provide a prophylactic measure against influenza for individuals with acute febrile illness.

Another goal of the present disclosure is to provide a treatment for the symptoms of influenza for individuals with acute febrile illness.

Another goal of the present disclosure is to provide a prophylactic measure against influenza for children with chronic medical conditions and children under the age of 2.

Another goal of the present disclosure is to provide a treatment for the symptoms of influenza for children with chronic medical conditions and children under the age of 2.

Another goal of the present disclosure is to provide a prophylactic measure against influenza for individuals with hypersensitivity and allergic reactions including hypersensitivity and allergies to residual egg proteins and other components of TIV and LAIV influenza vaccines including thimerosal and antibiotics.

Another goal of the present disclosure is to provide a prophylactic measure against influenza for those with a proportionately higher risk of Guillain-Barré Syndrome recurrence with TIV or LAW influenza vaccination or those with the inability to use LAIV after a history of GBS with TIV.

Another goal of the present disclosure is to provide a prophylactic measure against influenza with reduced risk of Guillain-Barré Syndrome.

Another goal of the present disclosure is to provide a prophylactic measure against influenza which reduces or eliminates viral shedding.

Another goal of the present disclosure is to provide a treatment for influenza which reduces or eliminates viral shedding.

Another goal of the present disclosure is to provide a prophylactic measure against influenza which reduces or eliminates LAIV and TIV side effects including, but not limited to: runny nose, headache, vomiting, myalgias, abdominal pain sore throat, asthma, and tiredness/weakness.

Another goal of the present disclosure is to provide a prophylactic measure against influenza which does not require forward prediction of virus strains and associated antigens to be effective.

Another goal of the present disclosure is to provide a prophylactic measure against influenza which does not require extensive prediction of virus strains and associated antigens to have extensive lead time to produce vaccine in sufficient quantities.

Another goal of the present disclosure is to provide a prophylactic measure against influenza with inherently lower risk factors thereby increasing prophylactic coverage of both at risk and general populations, thereby overcoming the reluctance of individuals who refuse to obtain a LAIV or TIV vaccination.

Another goal of the present disclosure is to provide a prophylactic measure against influenza which does not promote or contribute to drug resistance.

An additional goal of the disclosure is to demonstrate the use of fecal chymotrypsin level as a biomarker for the likelihood of an individual's susceptibility to influenza.

Yet another goal of the disclosure is to demonstrate the use of fecal chymotrypsin level as a biomarker for diagnosis of a compromised immune system, or for determining if an individual is likely to benefit from administration of a composition as described herein.

Yet another goal is to provide adjunctive compositions and methods to vaccination and/or anti-viral prophylactic medications, and/or adjunctive compositions and methods to therapeutic medications for the prevention and treatment of influenza.

It is a further goal of the present disclosure to provide viricidal and/or viristatic compositions comprising one or more digestive enzymes for use as or in disinfectants, sanitizers, detergents, and antiseptics, e.g., in hospitals, nursing homes, nurseries, daycares, schools, work environments, public transportation and restroom facilities, to reduce and/or destroy influenza viruses present in such settings. The surfaces can be large (e.g., operating room tables, doors, changing tables) or small (e.g., medical devices, door handles); inanimate (tables) or animate (hands, e.g., detergents for hand-washing). The compositions can thus be useful to treat surfaces to reduce or kill influenza virus thereon, and thereby prevent or reduce the spread of influenza.

Accordingly, provided herein is a method for preventing and/or treating Influenza comprising administering to the patient a therapeutically effective amount of a pharmaceutical composition comprising one or more digestive enzymes. In some embodiments, the pharmaceutical composition may be encapsulated; such encapsulated compositions may be referred to as enzyme preparations herein. In some embodiments, the pharmaceutical composition can be lipid-encapsulated.

In some embodiments, the one or more digestive enzymes comprise one or more enzymes selected from the group consisting of proteases, amylases, celluloses, sucrases, maltases, papain (e.g., from papaya), bromelain (e.g., from pineapple), hydrolases, and lipases. In some embodiments, the one or more digestive enzymes comprise one or more pancreatic enzymes. In some embodiments, the pharmaceutical composition comprises one or more proteases, one or more lipases, and one or more amylases. In some embodiments, the one or more proteases comprise chymotrypsin and trypsin.

The one or more digestive enzymes are, independently, derived from an animal source, a microbial source, a fungal source, or a plant source, or are synthetically prepared. In some embodiments, the animal source is a pig, e.g., a pig pancreas, or avian, e.g., "bird" proventriculus or small intestine.

In some embodiments, the pharmaceutical composition comprises at least one amylase, a mixture of proteases comprising chymotrypsin and trypsin, and at least one lipase. The pharmaceutical composition can further include papain, e.g., from papaya. In some embodiments, the pharmaceutical composition comprises per dose: amylases from about 10,000 to about 60,000 U.S.P, including 10,000, 15,000, 20,000, 25,000, 30,000, 35,000, 40,000, 45,000, 50,000, 55,000, and 60,000 U.S.P, along with all values in-between, proteases from about 10,000 to about 70,000 U.S.P, including 10,000, 15,000, 20,000, 25,000, 30,000, 35,000, 40,000, 45,000, 50,000, 55,000, 60,000, 65,000, and 70,000, along with all values in-between, lipases from about 4,000 to about 30,000 U.S.P, including, 4,000, 5,000, 10,000, 15,000, 20,000, 25,000, and 30,000, along with all values in-between, chymotrypsin from about 2 to about 5 mg including 2.0, 2.5, 3.0, 3.5, 4.0, 4.5, and 5.0 mg, along with all values in-between, trypsin from about 60 to about 100 mg including 50, 65, 70, 75, 80, 85,90, 95, and 100 mg, including all values in between; papain from about 3,000 to about 10,000 USP units including 3,000, 4,000, 5,000, 6,000, 7,000, 8,000, 9,000, and 10,000 USP, along with all values in between, and papaya from about 30 to about 60 mg, including 30, 35, 40, 45, 50, 55, and 60 mg, along with all values in between.

In some embodiments, the pharmaceutical composition comprises at least one protease and at least one lipase, wherein the ratio of total proteases to total lipases (in USP units) ranges from about 1:1 to about 20:1 including 1:1, 2:1, 3;1, 4:1, 5;1, 6:1, 7:1, 8:1, 9:1, 10:1, 11;1, 12;1, 13;1, 14:1, 15:1, 16;1, 17:1, 18:1, 19:1 and 20:1, long with all values in-between. In some embodiments, the ratio of proteases to lipases ranges from about 4:1 to about 10:1 including 4:1, 5:1, 6:1, 7:1, 8:1, 9:1, and 10:1, along with all values in-between.

In some embodiments, the one or more symptoms of influenza include: fever, headache, tiredness, cough, sore throat, runny or stuffy nose, body aches, diarrhea and vomiting, and a combination thereof.

In some embodiments, the pharmaceutical composition is a dosage formulation selected from the group consisting of: pills, tablets, capsules, microcapsules, mini-capsules, time released capsules, mini-tabs, sprinkles, and a combination thereof.

In some embodiments, a pharmaceutical composition comprises a core comprising one or more digestive enzymes, as described previously and a coating which comprises a crystallizable lipid. The core contains an amount of the one or more digestive enzymes effective for the prevention or treatment of Influenza. Among other properties, the coating protects the digestive enzymes from destabilizing factors such as solvents, heat, light, moisture and other environmental factors. The coating also provides controlled release of the enzymes when the encapsulate is exposed to a physiological conditions. In addition, in one aspect of this disclosure, the coated digestive enzyme preparations of this disclosure have improved pour properties, and improved taste and smell of the digestive enzyme particles. The coated digestive enzyme preparations can be used to obtain release at selected transit times or in selected locations of the gastrointestinal tract of mammals, as necessary.

In some embodiments, a specific blend of enzymes and lipids for enzyme administration to individuals for the prevention and/or treatment or influenza is provided.

In another embodiment a coated digestive enzyme preparation comprising (a) a core containing a digestive enzyme particle, where the enzyme present in an amount of from about 5% to 90% by weight of the particles, including 5%, 10%, 15%, 20%, 25%, 30%, 35%, 40%, 45%, 50%, 55%, 60%, 65%, 70%, 75%, 80%, 85%, and 90% by weight, along with all values in-between; and (b) a coating comprising a crystallizable lipid, wherein the coating continuously coats the core and the crystallizable lipid releases the enzyme upon exposure to physiological conditions.

In another embodiment a pharmaceutical composition comprising a therapeutically effective amount of an encapsulated enzyme preparation, which comprises (a) a core which comprises an amount of pancreatic or digestive enzymes effective for prophylaxis of influenza or treatment of the symptoms of influenza; and (b) coating comprising a crystallizable lipid.

In yet another embodiment an enzyme delivery system comprising an encapsulated enzyme preparation having particles which comprise: (a) a core comprising pancreatic or digestive enzymes present in an amount of from about 5% to 95% by weight of the particles, including 5%, 10%, 15%, 20%, 25%, 30%, 35%, 40%, 45%, 50%, 55%, 60%, 65%, 70%, 75%, 80%, 85%, 90% and 95% by weight along with all values in-between; and (b) a generally uniform coating to provide for controlled release of the enzymes, said coating comprising a crystallizable lipid. In yet another embodiment, the encapsulated enzyme preparation particles of the enzyme delivery system are non-aerosolizable.

In certain embodiments, the enzyme preparations according to this disclosure produce coated enzyme preparations characterized, for example, by controlled rates of release, reduction in aerosolization and safer administration, ability to be administered by a sprinkle/sachet delivery method, improved flow characteristics, enhanced shelf life and storage capacity, and other properties described herein. In other aspects, the coated enzyme preparation has improved pour properties which facilitate manufacturing and packaging processes, for example packaging in pouches and sachets.

Certain coated digestive enzyme preparations which comprise a coating of a crystallizable lipid and a digestive enzyme core have favorable release and activity profiles and permit site time specific and/or location specific targeted release along the GI tract for the prevention or treatment of influenza with digestive enzymes. In some aspects, the coated pancreatic/digestive enzyme preparations are prepared to obtain specific delivery times or specific regions within the human gastrointestinal (GI) tract. In some embodiments, the crystallizable lipid composition is hydrogenated soybean oil, but may be any suitable crystallizable lipid or lipid blend.

Some embodiments utilize stable enzyme preparations protected against the environment to reduce, for example, degradation and/or denaturation of the enzymes. This permits delivery of more accurate doses of the enzyme preparation to treated individuals. The coating can also, in some aspects, provide emulsification when the enzyme preparations are contacted with appropriate solvents, while also surprisingly providing for controlled release of the enzyme in the gastrointestinal (GI) system. The emulsification properties of the coating in a solvent allows for controlled release of the enzyme, preferably at selected locations in the GI tract, where enzyme utilization provides the most effective prophylaxis or treatment.

In another embodiment enzyme preparations are utilized with lipid coating and/or encapsulation of enzymes. The method of making the preparations comprises providing a crystallizable lipid, and coating screened pancreatic/digestive enzyme particles as described herein with the lipid. The digestive enzymes comprise 5% to 95% by weight of the coated enzyme preparations, including 5%, 10%, 15%, 20%, 25%, 30%, 35%, 40%, 45%, 50%, 55%, 60%, 65%, 70%, 75%, 80%, 85%, 90% and 95%, along with all values in-between;

The methods of this disclosure can be used to produce coated digestive enzyme preparations comprising digestive and/or pancreatic enzymes coated with a crystallizable lipid alone, or with a lipid blend to achieve a controlled rate of enzyme release, with increased release of the pancreatic/digestive enzyme upon exposure of the encapsulated preparation to a suitable solvent. Encapsulated pancreatic/digestive enzyme preparations having a coating comprising one or more monoglycerides exhibit increased release of the pancreatic/digestive enzyme upon exposure of the encapsulated composite to a solvent, such as water, while protecting against release in 0.1 N HCl.

In another embodiment, a method for administering the enzyme preparations includes administering compositions comprising one or more digestive enzymes as coated preparations. In some aspects, the disclosure relates to a prophylactic method comprising administering to a subject at least two doses of a composition comprising a therapeutically effective amount of an encapsulated digestive enzyme preparation comprising a core comprising a digestive enzyme; and a coating comprising a crystallizable lipid. Determination of whether a subject is in need of treatment with an effective amount of digestive enzymes may be based on a determination that the subject has an enzyme deficiency, and/or exhibits one or more symptoms associated with Influenza, and/or is diagnosed with Influenza, and/or is immune-compromised.

In another embodiment the pancreatic/digestive enzyme composites, preparations, enzyme delivery compositions or systems comprise no or fewer excipients, carriers, additives and/or extenders, and/or require the use of no or fewer solvents. In some embodiments, the coating comprises, consists of, or consists essentially of hydrogenated soybean oil, reducing exposure to potentially toxic substances and also reducing the possibility of allergy formation. In some embodiments the delivery of pancreative and/or digestive enzymes has improved safety of administration.

Also provided are methods for diagnosing patients based on fecal chymotrypsin levels. In one embodiment a method of diagnosing a patient comprises: obtaining a fecal sample from the patient, determining a level of chymotrypsin present in the fecal sample, in some cases wherein the determination is performed at 30° C., and diagnosing the patient as having a compromised immune system if the determined chymotrypsin level is less than a normal level (e.g., a control level).

In some embodiments, the fecal chymotrypsin level is between 8.4 and 4.2 U/gram. In some embodiments, the fecal chymotrypsin level is less than 4.2 U/gram. In some embodiments, the level of chymotrypsin present in the fecal sample is determined using an enzymatic photospectrometry method. In some embodiments, the method further comprises administering to the patient an effective amount of a pharmaceutical composition comprising one or more digestive enzymes if the patient is determined to have a compromised immune system, e.g., to treat or prevent influenza in the individual.

In some embodiments, the method further comprises determining if the administration of the pharmaceutical composition reduces the effects or symptoms of Influenza.

Also provided is a method of identifying a patient likely to benefit from administration of a pharmaceutical composition comprising one or more digestive enzymes comprising: obtaining a fecal sample from the patient, determining a level of chymotrypsin present in the fecal sample, in some cases wherein the determination is performed at 30° C., and identifying the patient as likely to benefit from administration of the pharmaceutical composition if the determined fecal chymotrypsin level is less than a normal (e.g., control level), e.g., in some embodiments 8.4 U/gram or less. In some embodiments, the patient is diagnosed with Influenza and/or is immune compromised. In some embodiments, the method further comprises determining if the patient exhibits one or more symptoms of Influenza. In some embodiments, the benefit comprises a reduction or amelioration of one or more symptoms associated with the Influenza. In some embodiments, the method further comprises administering to the patient an effective amount of a pharmaceutical composition comprising one or more digestive enzymes.

Also provided is a pharmaceutical composition comprising one or more digestive enzymes, wherein the one or more digestive enzymes comprise at least one lipase and at least one protease, and wherein the ratio of total proteases to total lipases (in USP units) ranges from about 1:1 to about 20:1 including 1:1, 2:1, 3;1, 4:1, 5;1, 6:1, 7:1, 8:1, 9:1, 10:1, 11;1, 12;1, 13;1, 14:1, 15:1, 16;1, 17:1, 18:1, 19:1 and 20:1 long with all values in-between. In some embodiments, the ratio of total proteases to total lipases ranges from about 4:1 to about 10:1 including 4:1, 5:1, 6:1, 7:1, 8:1, 9:1, and 10:1 along with all values in-between. In some embodiments, the pharmaceutical composition is lipid encapsulated.

Also provided is a pharmaceutical composition comprising at least one amylase, a mixture of proteases comprising chymotrypsin and trypsin, at least one lipase, and optionally papaya and/or papain. In some embodiments, the ratio of total proteases to total lipases ranges from about 1:1 to about 20:1 including 1:1, 2:1, 3;1, 4:1, 5;1, 6:1, 7:1, 8:1, 9:1, 10:1, 11;1, 12;1, 13;1, 14:1, 15:1, 16;1, 17:1, 18:1, 19:1 and 20:1 along with all values in-between.

The features and advantages described herein are not all-inclusive and, in particular, many additional features and advantages will be apparent to one of ordinary skill in the art in view of the drawings, specification, and claims.

DETAILED DESCRIPTION

The present disclosure provides pharmaceutical compositions comprising one or more digestive enzymes and methods of using the same for the treatment and/or prevention of Influenza. The present disclosure also provides compositions comprising one or more digestive enzymes and methods of using the same as antiseptics, detergents, disinfectants, and sanitizers, e.g., as viricidal and/or viristatic compositions to kill or attenuate the influenza virus. The compositions described herein include one or more digestive enzymes, which are postulated to assist in the reduction, weakening, or eradication of Influenza virus, and thus to prevent contraction of Influenza; and/or to ameliorate gastrointestinal dysfunction or to enhance the normal gastrointestinal function, in order to prevent contraction of Influenza or to treat Influenza (e.g., improve or ameliorate the symptoms or reduce the time course of the infection). In addition, the pharmaceutical compositions can be utilized to enhance immune system response for individuals with compromised immune systems and/or to augment immune system functions is nonimmuno-compromised individuals, e.g., to assist in the prevention or treatment of Influenza.

In certain embodiments, the pharmaceutical compositions can include one or more digestive enzymes, wherein the one or more digestive enzymes comprise at least one lipase and at least one protease, and wherein the ratio of total proteases to total lipases (in USP units) ranges from about 1:1 to about 20:1, including 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 and 20:1 along with all values in-between. In some cases, the ratio of total proteases to total lipases ranges from about 4:1 to about 10:1, including 4;1, 4;1, 6:1, 7:1, 8:1, 9:1, and 10:1 along with all values in-between. In some embodiments, the pharmaceutical composition is encapsulated, e.g., lipid-encapsulated. Enzyme preparations comprising one or more digestive enzymes useful for the methods described herein are disclosed in U.S. Ser. No. 12/386,051, incorporated herein by reference.

In some cases, a pharmaceutical composition for use herein comprises at least one amylase, at least one protease, and at least one lipase. In certain embodiments, the composition can comprise at least one amylase, at least two proteases, and at least one lipase. In certain embodiments the pharmaceutical composition includes multiple proteases, including, without limitation, chymotrypsin and trypsin. In certain embodiments, the composition can further include one or more hydrolases, papain, bromelain, papaya, celluloses, pancreatin, sucrases, and maltases.

The one or more enzymes can be independently derived from animal, plant, fungal, microbial, or synthetic sources. In some embodiments, the one or more enzymes are derived from pig, e.g. pig pancreas or avian "bird" proventriculus or small intestine.

One exemplary formulation for the prevention of Influenza or treatment of symptoms of Influenza is as follows:
Amylase 10,000-60,000 U.S.P
Protease 10,000-70,000 U.S.P
Lipase 4,000-30,000 U.S.P
Chymotrypsin 2-5 mg
Trypsin 60-100 mg
Papain 3,000-10,000 USP units/mg
Papaya 30-60 mg Additional formulations comprising one or more digestive enzymes may be advantageous including formulations in which the ratio of total proteases to total lipases (in USP units) is from about 1:1 to about 20:1, including 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 and 20:1 along with all values in-between. In some embodiments, the ratio of total proteases to total lipases is from about 4:1 to about 10:1 including 4:1, 5:1, 6:1, 7:1, 8:1, 9:1, and 10:1 along with all values in-between. Such formulations are useful for the prevention of Influenza or treating symptoms of Influenza, or the enhancement of immune system functions.

The pharmaceutical compositions can be formulated in dosage forms for any route of administration, including oral, parenteral, IV, inhalation, and buccal dosage formulations. In certain embodiments, a dosage formulation may be administered by an oral preparation including, but not limited to, an encapsulated tablet, mini-tabs, microcapsule, mini-capsule, time released capsule, sprinkle, powder or other methodology. In one embodiment, the oral preparation is encapsulated using one or more lipids. Alternatively, the oral preparation may be encapsulated using enteric coating or organic polymers. A formulation may also be prepared using Prosolv® technology, direct compression, dry granulation, wet granulation, and/or a combination of these methods.

Fecal chymotrypsin level is a sensitive, specific measure of proteolytic activity, see, e.g. U.S. Pat. No. 6,660,831, incorporated by reference herein. Normal levels of chymotrypsin are typically considered to be greater than 8.4 U/gram. Decreased values (less than 4.2 U/gram) suggest diminished pancreatic output (pancreatic insufficiency), hypoacidity of the stomach or cystic fibrosis. Elevated chymotrypsin values suggest rapid transit time, or less likely, a large output of chymotrypsin from the pancreas.

For the fecal chymotrypsin test, a stool sample can be collected from each of the subjects. Each stool sample can be analyzed using an enzymatic photospectrometry analysis to determine the level of fecal chymotrypsin in the stool; in some cases the assay is performed at 30° C., see, e.g. U.S. Pat. No. 6,660,831, incorporated by reference herein. Alternatively, other methods, such as the colorimetric method, use of substrates, use of assays, and/or any other suitable method may be used to measure the fecal chymotrypsin levels. The levels of fecal chymotrypsin in the samples e.g., of individuals suspected of or diagnosed as having a compromised immune system, are compared to the levels of fecal chymotrypsin in normal or control individuals (e.g., individuals not suspected or diagnosed with a compromised immunes system), to determine if the individuals would benefit from the administration of a composition as described herein.

The nature of the human digestive tract creates challenges for the delivery of digestive enzymes to patients including the general population, those with compromised immune systems, or those with influenza. Multiple temperature and pH changes over the course of the digestive tract make specific delivery a necessity and a challenge. For instance, pH as low as 1 is encountered in the stomach, but rapidly increases to a more basic pH of 5-6 in the proximal small intestine. For example, generally the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach which changes rapidly to a more basic pH of 5-6 in the proximal small intestines, calls for a specific delivery method depending upon where the enzyme is to be delivered. For veterinary applications, a specific delivery location may also be necessary, depending on the animal to be treated.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and shortening shelf life, leading to inaccurate dosing. Denaturization or destabilization of the enzymes can reduce their effectiveness by reducing the dose of active enzymes to less than the amount needed for effective treatment. Alternatively, attempting to compensate for the denaturization or destabilization by increasing the dose to ensure an effective level of active enzyme, could risk an overdose or overfilling a capsule or other dosage form. To protect and stabilize the compositions from unfavorable conditions, the digestive enzymes may be coated or encapsulated in a continuous coating containing a crystallizable lipid.

Manufacturers of enzyme preparations have used enteric coatings to deliver lipases in individuals requiring administration of lipases, such as individuals with cystic fibrosis.

Coatings in the digestive/pancreatic enzyme preparations create a barrier to degradation and denaturation, and allow more accurate levels of active enzymes to reach the treated individuals.

For example, a lipid coating of this disclosure provides a significant barrier to moisture, heat, humidity and exposure to light by allowing for a physical barrier as well as one that prevents and or reduces hydrolysis. The coated enzyme preparations undergo less hydrolysis as a result of protection from moisture in the environment by the lipid coating. As a result of the present disclosure, pancreatic/digestive enzymes are provided which can tolerate storage conditions (e.g., moisture, heat, oxygen, etc.) for long periods of time thus enabling extended shelf life. The coating of the encapsulated enzyme preparation protects the enzyme from the environment and provides emulsification in a solvent without detracting from the abrasion resistance of the coating.

In some embodiments, the coatings on the digestive enzyme particle cores are preferably continuous coatings. By "continuous," it is meant that the pancreatic/digestive enzyme is uniformly protected. The continuous coating of the fully surrounds or encapsulates the pancreatic/digestive enzymes. The encapsulation provides protection of the pancreatic/digestive enzyme from conditions such as moisture, temperature, and conditions encountered during storage.

As discussed, the encapsulation can provide controlled release of the digestive enzymes. The emulsification properties of the coating in a solvent allows for controlled release of the enzyme in the gastrointestinal system, preferably the region of the GI tract where the enzymes are to be utilized. In some embodiments, the dissolution profile may be about 30, 35, 40, 45, 50, 55, 60, 65, 70, 75, 80, 85 or 90 minutes. Dissolution profiles may be obtained using methods and conditions known to those of skill in the art. For example, dissolution profiles can be determined at various pH's, including pH. 1, 2, 3, 4, 5, 6, 7, 8, 9, 10.

"Encapsulate" as used herein means that the coating completely surrounds the pancreatic/digestive enzyme. In a population of encapsulated particles, encapsulated enzyme preparations may include contaminating or small portion of particles with a substantially continuous coating as long as the release profiles of the encapsulated particles are not significantly altered. A coated or encapsulated particle may contain one or more digestive enzyme particles enveloped in one coating to form one coated or encapsulated digestive enzyme particle in the coated or encapsulated digestive enzyme preparation.

The crystallizable lipid is any lipid or wax, lipid or wax mixture, or blend of lipid and/or waxes, where the crystalliable lipid forms a solid coating via crystallization at typical storage temperatures. The crystallizable lipid can be a vegetable or animal derived-lipid. In some embodiments, the crystallizable lipid is emulsifiable upon contact with physiological conditions and consists essentially of, or comprises one or more monoglycerides, diglycerides or triglycerides, or other components including, for example, emulsifiers found in hydrogenated vegetable oils. In another embodiment the crystallizable lipid is a non-polar lipid, for example hydrogenated soybean oil As used herein, animal and/or vegetable "derived" lipids can include fats and oils originating from plant or animal sources and/or tissues, and/or synthetically produced based on the structures of fats and oils originating from plant or animal sources. Lipid material may be refined, extracted or purified by known chemical or mechanical processes. Certain fatty acids present in lipids, termed essential fatty acids, must be present in the mammalian diet. The lipid may, in some embodiments, comprise a Type I USP-National Formulary vegetable oil.

The digestive enzyme used in the present disclosure can be, for example, any combination of digestive enzymes of a type produced by the pancreas, including, but not limited to digestive enzymes from a pancreatic source or other sources. The scope of the disclosure is not limited to pancreatic enzymes of porcine origin, but can be of other animal, microbial, or plant origin as well as those which are synthetically derived. The digestive enzyme may be derived from mammalian sources such as porcine-derived digestive enzymes. The enzyme may include one or more enzymes, and can also be plant derived, synthetically derived, recombinantly produced in microbial, yeast, fungal or mammalian cells, and can include a mixture of enzymes from one or more sources. Digestive enzymes, can include, for example, one or more enzymes from more or more sources mixed together. This includes, for example, the addition of single digestive enzymes to digestive enzymes derived from pancreatic sources in order to provide appropriate levels of specific enzymes that provide more effective treatment for a selected disease or condition. One source of digestive enzymes can be obtained, for example, from Scientific Protein Laboratories (see Table 6). The digestive enzyme may be, for example a pancreatin/pancrelipase composition. In one embodiment, the digestive enzymes will comprise or consist essentially of 25 USP units/mg protease, 2 USP Unit/mg, and 25 USP Units/mg amylase.

In some embodiments, the digestive enzyme particles used as cores in the present disclosure include digestive enzyme particles where about 90% of the particles are between about #40 and #140 USSS mesh in size, or between about 105 to 425 µm, including 105, 125, 150, 175, 200, 225, 250, 275, 300, 325, 350, 375, 400, and 425 µm or where at least about 75% of the particles are between about #40 and #80 mesh, or about 180 to 425 µm in size. Particles between #40 and #140 mesh in size pass through #40 mesh but do not pass through #140 mesh. The coated or encapsulated digestive enzyme particles in one embodiment of this disclosure may comprise less than about 35, 30, 25, 20, 15 or 10% of the particles which can be sieved through #100 mesh (150 µm). In some embodiments, the term "non-aerosolizable" refers to a coated or encapsulated enzyme preparation where less than about 20% or less than about 15% of the particles can be sieved through #100 mesh (150 µm). The encapsulated digestive enzyme preparation can be an encapsulated digestive enzyme composite where the digestive enzyme particles contain two or more enzymes.

The minimum amount of pancreatic enzyme present in the core can vary, and in some embodiments is at least about 5% active enzymes by weight of the coated enzyme preparation, but in other embodiments may be at least about 30%, or at least about 50% by weight. The maximum amount of pancreatic/digestive enzyme present in the composite can vary, and in some cases is at most about 95% by weight, and in other embodiments at most about 90%, 85%, 80%, 75% or 70% of the coated enzyme preparation. In other embodiments, the amount of pancreatic enzyme present in the composite is about 10%, 15%, 20%, 25%, 35%, 40%, 45%, 55%, 60%, 65%, 70%, 72.5%, 75%, 77.5%, 80%, 82.5%, 87.5%, or 92.5% by weight or anywhere in between.

The composition which contains the encapsulated digestive enzyme preparation or composite can be delivered as a sprinkle, powder, capsule, tablet, pellet, caplet or other form. Packaging the encapsulated enzyme preparations in an enzyme delivery system that further comprises single dose sachet-housed sprinkle preparations allows for ease of delivery, and accurate dosing of the enzyme, by allowing a specific amount of enzyme to be delivered in each dosing. Allowing for specific unit dosing of an enzyme preparation which maintains the enzyme activity within specific stability parameters in an enhancement over other sprinkle formulations, which are housed, in a multi-unit dosing form that allows for air, moisture and heat to depredate and denature the enzyme preparation. In a preferred embodiment the powder or sachet is housed in a trilaminar foil pouch, or similar barrier to keep out moisture and to protect the enzyme preparation from adverse environmental factors.

Further, in some embodiments, the lipid encapsulation methodology reduces the aerosolization of the enzyme preparation that may be caustic to an individual if inhaled through the lungs or the nose. The lipid encapsulation reduces aerolization and the potential for caustic burn, aspiration, and/or aspiration pneumonias in receivers and administrators of the enzyme preparation, thereby reducing the potential for illness in those already compromised by influenza or reduced immune system functionality, and leading to safer administration.

As used herein, the term "non-aerosolizable" will be used to refer to a coated or encapsulated enzyme preparation where substantially all of the particles are large enough to eliminate or reduce aerosolization upon pouring of the coated enzyme preparation compared to uncoated enzyme particles. For example, the term "non-aerosolizable" may refer to a coated or encapsulated enzyme preparation where at least about 90% of the particles are between about #40 and #140 mesh in size, or between about 106 to 425 μm, or where at least about 75% of the particles are between about #40 and #80 mesh, or about 180 to 425 μm. The term "non-aerosolizable" may also refer to a coated or encapsulated enzyme preparation where less than about 35, 30, 25, 20, 15 or 10% of the particles can be sieved through #100 mesh (150 μm). In some embodiments, the term "non-aerosolizable" refers to a coated or encapsulated enzyme preparation where less than about 20% or less than about 15% of the particles can be sieved through #100 mesh (150 μm).

The choice of suitable enzymes and of suitable lipid coatings, including choice of the type or amount of enzymes or coating, are guided by the specific enzyme needs of the individual to be treated.

Additives can be blended with a crystallizable lipid. Selection of the lipid(s) and additives will control the rate of release of the bioactive substance. In the case of the digestive and or pancreatic enzymes, the lipid can be chosen to release the bioactive substance in the area of the digestive tract selected for release to optimize treatment.

The disclosure further relates to the administering of the coated and/or encapsulated enzyme preparation in a sachet or pouch preparation for ease of delivery to children and adults. In some embodiments, the disclosure specifically relates to the administration of a coated enzyme particle preparation, housed in a sachet or pouch. This facilitates administration, including but not limited to, administration in food or drink, direct administration into the oral cavity, or administration directly into the GI system through an NG-tube, G-tube or other GI entrances or deliveries.

In some embodiments, each dose contains about 100 to 1500 mg of coated or encapsulated enzyme preparation, and each dose may contain about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 mg of coated or encapsulated enzyme preparation. "About" can include 80 to 125% of the recited preparation. Each dose may also be plus or minus 10% of the recited weight. In one embodiment each does will have a protease activity of not less than about 156 USP units/mg plus or minus 10%. The protease activity may also be not less than about 100, 105, 110, 115, 120, 125, 130, 135, 140, 145, 150, 155, 160, 165, 170, 175, 180, 185, 190, 195, or 200 USP units/mg.

In other embodiments, the disclosure relates to methods of treatment comprising administering to a subject, at least two doses of a composition comprising a therapeutically effective amount of the coated digestive enzyme preparations for the prophylaxis or treatment or influenza. In certain embodiments, about 80% of the enzyme is released by about 30 minutes in a dissolution test performed at pH 6.0. In other embodiments, about 80% of the enzyme is released by about 30 minutes after the coated digestive enzyme preparations reach the small intestine.

In other embodiments, the disclosure relates to methods of treatment comprising administering to a subject, at least three doses of a composition comprising a therapeutically effective amount of the coated digestive enzyme preparations for the prophylaxis or treatment or influenza. In certain embodiments, about 80% of the enzyme is released by about 30 minutes in a dissolution test performed at pH 6.0. In other embodiments, about 80% of the enzyme is released by about 30 minutes after the coated digestive enzyme preparations reaches the small intestine.

Another embodiment of the disclosure relates to the improvement of delivery of enzymes to humans by reducing the use of excipients, extenders and solvents currently used in the preparations for delivery of digestive enzymes to humans. For example, the encapsulated digestive enzyme preparation may contain only one excipient, which increases the safety of administration by decreasing the chance of an allergic response. In one embodiment, the excipient is hydrogenated soybean oil.

The lipid coating surprisingly does not appear to be reduced or destroyed by HCl (hydrochloric acid) present in the stomach, thereby protecting the enzyme from degradation following administration until the enzyme preparation reaches its target region in the GI tract. Further the lipid coat reduces the exposure of the enzyme to attack by water, thereby reducing hydrolysis, and further protecting the digestive enzymes from degradation. In addition, an excipient containing only lipid can be used to coat or encapsulate digestive enzyme particles containing lipase.

The disclosure therefore relates to improvement of the delivery of digestive enzymes to humans or animals based specifically upon needed delivery times, and dissolution profiles. For example, in certain aspects of the disclosure, the rate of release and dissolution characteristics are unique to the lipid encapsulations of this disclosure For prophylaxis of influenza or treatment of patients with influenza or immune compromised individuals who require delivery of protease enzymes for effective treatment, the lipid encapsulate can be modified to deliver the protease during an earlier transit time window, in the proximal small intestine, to optimize virion protein digestion. In another example, for elderly patients with slower GI transit times, still another release profile may be advantageous to deliver enzymes for effective treatment. The lipid and/or additive selection will be made to obtain enzyme release at later times after administration. In veterinary applications, still another release profile may be necessary.

The present disclosure also relates to methods of making the enzyme preparations by lipid coating and/or encapsulation of pancreatic and/or digestive enzymes. The methods comprise providing a crystallizable lipid, and coating pancreatic/digestive enzyme particles with the lipid, where the pancreatic/digestive enzymes comprise 5-90% including 5, 10, 15, 20, 25, 30, 35, 40, 45, 50, 55, 60, 65, 70, 75, 80, 85, and 90% along with all values in-between of the coated enzyme preparations by weight. In some aspects the uncoated pancreatic/digestive enzyme particles have a size range of about 105-425 μm including 105, 125, 150, 175, 200, 225, 250, 275, 300, 325, 350, 375, 400, and 425 μm along with all values in-between.

In one embodiment, the disclosure relates to a method of preparing an encapsulated digestive enzyme preparation, the method comprising (a) screening uncoated digestive enzyme particles to obtain particles of a suitable size for encapsulation; and (b) coating the screened digestive enzyme particles with a crystallizable lipid to form coated or encapsulated digestive enzymes containing a core which contains the pancreatic/digestive enzyme and a coating which contains the crystallizable lipid. In some embodiments, the encapsulated digestive enzyme preparation is a controlled release digestive enzyme preparation, which may have enhanced flow properties.

Screening of the particles may include quality control steps to improve the activity, appearance or particle size of the digestive enzyme. For example, the particles may be analyzed to determine enzyme activity content, and/or visualized using chromatographic, microscopic or other analytical methods. The particles may also be screened to obtain particles of a suitable size for encapsulation by removing particles that are too fine or too large. For example, the particles may be sieved to obtain particles of a suitable size or more uniform size range for encapsulation. As a further example, the particles may be sieved through USSS #40 mesh and through USSS #140 mesh. Particles that pass through the #40 mesh but are retained by the #140 mesh are of an appropriate size range for coating or encapsulation. Particles may also be screened by sieving through USSS #140, #120, #100, #80, #70, #60, #50, #45, or #40 mesh, or any combination thereof.

In some embodiments, the lipid should be present in the preparation at a minimum amount of about 5% by weight of the encapsulated composite, preferably about 30%, and more preferably about 50% by weight of the encapsulated composite. The maximum amount of pancreatic/digestive enzyme present in the encapsulated composite is about 95% by weight of the composite, preferably about 90%, and more preferably about 85% of the encapsulated composite. The crystallizable lipid can be any lipid or lipid-derived material that creates a solid coating around the digestive enzyme substrate. This lipid coating releases the digestive enzyme in the GI tract. The lipid coating may be emulsifiable in the GI tract, releasing the digestive enzyme.

The crystallizable lipid can be derived from animal or vegetable origins, such as, for example, palm kernel oil, soybean oil, cottonseed oil, canola oil, and poultry fat, including hydrogenated type I vegetable oils and waxes. In some embodiments, the lipid is hydrogenated. The lipid can also be saturated or partially saturated. Examples of crystallizable lipids include, but are not limited to, monoglycerides, diglycerides, triglycerides, fatty acids, esters of fatty acids, phospholipids, salts thereof, and combinations thereof. The crystallizable lipid can be an emulsifiable lipid.

"Emulsifiable lipids" as used herein means those lipids which contain at least one hydrophilic group and at least one hydrophobic group, and have a structure capable of forming a hydrophilic and hydrophobic interface. These chemical and/or physical properties, mentioned above, of an emulsifiable lipid permit emulsification. Examples of interfaces include, for example, micelles and bilayers. The hydrophilic group can be a polar group and can be charged or uncharged.

The crystallizable lipid which is emulsifiable is preferably a food grade emulsifiable lipid. Some examples of food grade emulsifiable lipids include sorbitan monostearates, sorbitan tristcaratcs, calcium stearoyl lactylates, and calcium stearoyl lactylates. Examples of food grade fatty acid esters which are emulsifiable lipids include acetic acid esters of mono- and diglycerides, citric acid esters of mono- and di-glycerides, lactic acid esters of mono- and di-gylcerides, polyglycerol esters of fatty acids, propylene glycol esters of fatty acids, and diacetyl tartaric acid esters of mono- and diglycerides. Lipids can include, for example, hydrogenated soy oil.

Any emulsifiable lipid may be used in the methods and products of this disclosure. In certain embodiments the emulsifiable lipid used will produce non-agglomerating, non-aerosolizing enzyme preparation particles.

The coating of the enzyme with the lipid allows for the enzyme to become more uniform in size and shape, but reduces the jagged edges associated with the raw enzyme, and allows for ease of administration and ease of manufacturing, as the flow properties associated with the covered enzyme will allow for the manufacturing machinery to easily fill the appropriate containers.

The inclusion of one or more additives with an emulsifiable lipid of the present disclosure is used to control emulsification of the coating and release of the enzyme. For example, the additive, triglyceride, can be blended with monoglycerides (e.g., an emulsifiable lipid), to control emulsification of the coating and thus control (e.g., decrease) the rate of release of the enzyme from the composite. As a further example, one or more additives, such as a diglyceride and a triglyceride can be blended with the emulsifiable lipid to control the rate of release of the enzyme. Hydrogenated vegetable oils may contain emulsifying agents, such as soy lecithin or other components.

Properties including mechanical strength, melting point, and hydrophobicity can be considered when choosing a suitable lipid coating for the digestive enzyme. Lipids having lower melting points or more polar, hydrophilic properties were generally less suitable for encapsulation because they resulted in product that would cake under accelerated storage stability conditions. Enzyme preparations made using, for example, hydrogenated soy oil, hydrogenated castor wax, and carnauba wax all demonstrated good pouring and no caking.

The wax can be paraffin wax; a petroleum wax; a mineral wax such as ozokerite, ceresin, or montan wax; a vegetable wax such as, for example, camuba wax, bayberry wax or flax wax; an animal wax such as, for example, spermaceti; or an insect wax such as beeswax.

Additionally, the wax material can be an ester of a fatty acid having 12 to 31 carbon atoms and a fatty alcohol having 12 to 31 carbon atoms, the ester having from a carbon atom content of from 24 to 62, or a mixture thereof. Examples include myricyl palmitate, cetyl palmitate, myricyl cerotate, cetyl myristate, ceryl palmitate, ceryl certate, myricyl melissate, stearyl palmitate, stearyl myristate, and lauryl laurate.

The solvent in which a lipid emulsifies can be an aqueous solvent. The aqueous solvent interacts with the hydrophilic groups present in the emulsifiable lipid and disrupts the continuity of the coating, resulting in an emulsion between the aqueous solvent and the lipids in the coating, thus releasing the bioactive substance from the composites.

Other additives for inclusion in the compositions described herein can be determined by those having ordinary skill in the art, and will be based on a number of features, including intended application, e.g., human vs. veterinary applications; desired release profile; desired pharmacokinetics; safety; stability; physical characteristics (smell, color, taste, pour, aerosilization). Suitable formulation ingredients, excipients, binders, bulking agents, flavorants, colorants, etc. can be determined and evaluated by methods known to those having ordinary skill.

In one aspect of the disclosure, the method comprises using the enzyme formulations to treat individuals that have an enzyme deficiency. The enzyme deficiency could be determined by any method used in determining or diagnosing an enzyme deficiency. In one aspect the determination or diagnosis may be made by evaluating symptoms, including eating habits, self-imposed dietary restrictions, symptoms of eating disorders and/or gastrointestinal disorders. In other aspects, the determination may be made on the basis of a biochemical test to detect, for example, levels or activities of enzymes secreted, excreted or present in the GI tract, and/or by determining the presence of a mutation in a gene or aberrant expression of a gene encoding one or more digestive enzymes. The enzyme deficiency may also be determined, for example, by detecting a mutation or aberrant expression of a gene encoding a product regulating or otherwise affecting expression or activity of one or more digestive enzymes.

The present disclosure also provides viricidal and/or viristatic compositions comprising one or more digestive enzymes for use as or in disinfectants, sanitizers, detergents, and antiseptics, e.g., in hospitals, nursing homes, nurseries, daycares, schools, work environments, public transportation and restroom facilities, to reduce and/or destroy influenza viruses present in such settings. The surfaces can be large (e.g., operating room tables, doors, changing tables) or small (e.g., medical devices, door handles); inanimate (tables) or animate (hands, e.g., detergents for hand-washing). The compositions include one ore more digestive enzymes, and optionally additives customarily used in antiseptics, disinfectants, sanitizers and detergents. The viricidal and viristatic compositions can be encapsulated enzyme compositions, as described previously, to increase stability and shelf-life.

Disinfectants are antimicrobial agents that are applied to non-living objects to destroy microorganisms, the process of which is known as disinfection. Disinfectants should generally be distinguished from antibiotics that destroy microorganisms within the body, and from antiseptics, which destroy microorganisms on living tissue. Sanitizers are substances that reduce the number of microorganisms to a safe level. One official and legal version states that a sanitizer must be capable of killing 99.999%, known as a 5 log reduction, of a specific test population, and to do so within 30 seconds. The main difference between a sanitizer and a disinfectant is that at a specified use dilution, the disinfectant must have a higher kill capability compared to that of a sanitizer. Very few disinfectants and sanitizers can sterilize (the complete elimination of all microorganisms), and those that can depend entirely on their mode of application.

The choice of the disinfectant to be used depends on the particular situation. Some disinfectants have a wide spectrum (kill nearly all microorganisms), whilst others kill a smaller range of disease-causing organisms but are preferred for other properties (they may be non-corrosive, non-toxic, or inexpensive).

The relative effectiveness of disinfectants can be measured by comparing how well they do against a known disinfectant and rate them accordingly. Phenol is the standard, and the corresponding rating system is called the "Phenol coefficient". The disinfectant to be tested is compared with phenol on a standard microbe (usually Salmonella typhi or Staphylococcus aureus). Disinfectants that are more effective than phenol have a coefficient >1. Those that are less effective have a coefficient <1. For example, the Rideal-Walker method gives a Rideal-Walker coefficient and the U.S. Department of Agriculture method gives a U.S. Department of Agriculture coefficient.

To calculate phenol coefficient, the concentration of the test compound at which the compound kills the test organism in 10 minutes, but not in 5 minutes, is divided by the concentration of phenol that kills the organism under the same conditions. The phenol coefficient may be determined in the presence of a standard amount of added organic matter or in the absence of organic matter.

A detergent is a material intended to assist cleaning. The term is sometimes used to differentiate between soap and other surfactants used for cleaning where soap is a surfactant cleaning compound, typically used for personal or minor cleaning.

Detergents and soaps are used for cleaning because pure water can't remove oily, organic soiling. Soap cleans by acting as an emulsifier. Basically, soap allows oil and water to mix so that oily grime can be removed during rinsing. Detergents were developed in response to the shortage of the animal and vegetable fats used to make soap during World War I and World War II. Detergents are primarily surfactants, which could be produced easily from petrochemicals. Surfactants lower the surface tension of water, essentially making it 'wetter' so that it is less likely to stick to itself and more likely to interact with oil and grease.

Modern detergents contain more than surfactants. Cleaning products may also contain enzymes to degrade protein-based stains, bleaches to de-color stains and add power to cleaning agents, and blue dyes to counter yellowing. Like soaps, detergents have hydrophobic or water-hating molecular chains and hydrophilic or water-loving components. The hydrophobic hydrocarbons are repelled by water, but are attracted to oil and grease. The hydrophilic end of the same molecule means that one end of the molecule will be attracted to water, while the other side is binding to oil. Neither detergents nor soap accomplish anything except binding to the soil until some mechanical energy or agitation is added into the equation. Swishing the soapy water around allows the soap or detergent to pull the grime away from clothes or dishes and into the larger pool of rinse water. Rinsing washes the detergent and soil away. Warm or hot water melts fats and oils so that it is easier for the soap or detergent to dissolve the soil and pull it away into the rinse water. Detergents are similar to soap, but they are less likely to form films (soap scum) and are not as affected by the presence of minerals in water (hard water).

Detergents, especially those made for use with water, often include different components such as Surfactants to 'cut' (dissolve) grease and to wet surfaces, abrasives to scour, substances to modify pH or to affect performance or stability of other ingredients, acids for descaling or caustics to break down organic compounds, water softeners to counteract the effect of "hardness" ions on other ingredients, oxidants (oxidizers) for bleaching, disinfection, and breaking down organic compounds, non-surfactant materials that keep dirt in suspension, enzymes to digest proteins, fats, or carbohydrates in stains or to modify fabric feel, ingredients that modify the foaming properties of the cleaning surfactants, to either stabilize or counteract foam, ingredients to increase or decrease the viscosity of the solution, or to keep other ingredients in solution, in a detergent supplied as a water solution or gel, ingredients that affect aesthetic properties of the item to be cleaned, or of the detergent itself before or during use, such as optical brighteners, fabric softeners, colors, perfumes, etc., ingredients such as corrosion inhibitors to counteract damage to equipment with which the detergent is used, ingredients to reduce harm or produce benefits to skin, when the detergent is used by bare hand on inanimate objects or used to clean skin, and preservatives to prevent spoilage of other ingredients.

There are several factors that dictate what compositions of detergent should be used, including the material to be cleaned, the apparatus to be used, and tolerance for and type of dirt.

Modern detergents may be made from petrochemicals or from oleochemicals derived from plants and animals. Alkalis and oxidizing agents are also chemicals found in detergents. The most used disinfectants are those applying: active chlorine (i.e., hypochlorites, chloramines, dichloroisocyanurate and trichloroisocyanurate, wet chlorine, chlorine dioxide etc.): active oxygen (peroxides, such as peracetic acid, potassium persulfate, sodium perborate, sodium percarbonate and urea perhydrate); iodine (iodpovidone (povidone-iodine, Betadine), Lugol's solution, iodine tincture, iodinated nonionic surfactants); concentrated alcohols (mainly ethanol, 1-propanol, called also n-propanol and 2-propanol, called isopropanol and mixtures thereof; further, 2-phenoxyethanol and 1- and 2-phenoxypropanols are used); phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof); cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds, such as chlorhexidine, glucoprotamine, octenidine dihydrochloride etc.); strong oxidizers, such as ozone and permanganate solutions; heavy metals and their salts, such as colloidal silver, silver nitrate, mercury chloride, phenylmercury salts, copper sulfate, copper oxide-chloride etc. Heavy metals and their salts are the most toxic, and environment-hazardous bactericides and therefore, their use is strongly oppressed or canceled; further, also properly concentrated strong acids (phosphoric, nitric, sulfuric, amidosulfuric, toluenesulfonic acids) and alkalis (sodium, potassium, calcium hydroxides), such as of pH<1 or >13, particularly under elevated temperature (above 60° C.), kills bacteria.

Antiseptics (from Greek αντι—anti, "'against"+ σηπτικός—septikos, "putrefactive") are antimicrobial substances that are applied to living tissue/skin to reduce the possibility of infection, sepsis, or putrefaction. They should generally be distinguished from antibiotics that destroy bacteria within the body, and from disinfectants, which destroy microorganisms found on non-living objects.

A composition for use as a sanitizer, detergent, disinfectant, or antiseptic can, in some cases, be diluted in a suitable diluent such as saline, phosphate buffered solutions, and other pH stabilized aqueous solutions, and can be used in combination with other sanitizers, detergents, disinfectants, or antiseptics, such as alcohols, quaternary ammonium compounds, boric acid, chlorhexidine gluconate, iodine, octenidine dihydrochloride, and sodium chloride.

Recent USDA Studies in Swine

Recent experimental test results from the Unites States Department of Agriculture serve to verify the efficacy of porcine intestinal immune systems against various H1N1 and other influenza diseases.

Experiment 1:

Four Pig Pathogenesis Study with the 2009 A/H1N1 Influenza A Virus.

Purpose of Study:

An important concern is to address whether meat, blood and tissue from pigs infected with the new 2009 H1N1 Influenza A Virus is free of infectious virus.

Experiment:

Four 5-week-old cross-bred pigs from a herd free of swine influenza virus (SIV) and porcine reproductive and respiratory syndrome virus (PRRSV) were housed in containment facilities and cared for in compliance with the Institutional Animal Care and Use Committee of the National Animal Disease Center (NADC).

Pigs were inoculated intra-tracheally with an infective dose of the 2009 H1N1 Influenza A Virus isolated from persons in California (A/CA/04/2009) obtained from the Center for Disease Control and Prevention (CDC).

Pigs were observed daily for clinical signs of disease. Nasal swabs were taken on 0, 1, 2, 3, 4, and 5 days post infection (dpi) to evaluate nasal shedding. Pigs were humanely euthanized on 5 dpi, which is considered the peak of infection in the NADC porcine SIV challenge model, to evaluate lung lesions and viral load in the lung and tissues. Fresh samples were taken from lung, tonsil, inguinal lymph node, liver, spleen, kidney, skeletal muscle (ham), and colon contents (feces), and examined using both real time RT-PCR and virus isolation (VI) techniques, which are the most sensitive and specific tools to detect the presence of viral nucleic acid and live virus, respectively.

Results:

Tissues outside the respiratory tract were found to be negative by VI at 5 days post infection. Only respiratory tract samples were positive by both methods (real time RT-PCR and VI). The inguinal lymph node from one pig and serum from two pigs were positive by real time RTPCR. However, lymph node and serum samples from all pigs were negative by VI. By contrast, all day 5 post infection nasal swabs and lung lavage fluids were positive by real time RT-PCR and VI, and lung tissue homogenates from all four pigs were positive by real time RT-PCR and 2/4 samples positive by VI.

Conclusion:

Live 2009 A/H1N1 Influenza A Virus was only detected in the respiratory tract of infected pigs and the virus does not appear to spread and replicate in other tissues based on the day 5 post infection samples.

In addition, while not bound by theory, the efficacy of porcine enzymes may be enhanced by vaccinating pancreatic porcine donors with Trivalent inactivated influenza vaccine (TIV) or Live attenuated influenza vaccine LAIV. Current test results suggest that vaccinated pigs demonstrate a pre-existing immunity to certain currently circulating H1N1 SW strains may protect against an outbreak virus.

Experiment II

Recent Results from Studies with the 2009 A/H1N1 Influenza A VirusProject 1: Serologic cross-reactivity of serum samples from U.S pigs against the new 2009H1N1 influenza virus.

Purpose of Study:

An important concern is to address whether U.S commercial swine herds are susceptible to the 2009 A/H1N1 influenza viruses isolated from persons in California, New York, and Mexico.

Experiment:

Three 2009 A/H1N1 influenza A viruses isolated from persons in 2009 in California A/CA/04/2009), New York (A/NY/18/2009), and Mexico (A/Mexico/4108/2009) were obtained from the Centers for Disease Control and Prevention (CDC) and grown in vitro (i.e., in a permissive cell line).

A standard hemagglutination inhibition (HI) test was used to investigate antigenic relatedness between these three 2009 A/H1N1 influenza A viruses and 19 H1 Swine Influenza Virus (SIV) strains known to be circulating in U.S. swine herds or with SW strains used for five licensed U.S H1N1 SW vaccines. Antigenic relatedness would be predicted on the basis of how well these antisera could inhibit the three 2009 A/H1N1 influenza A viruses from agglutinating (clumping) red blood cells. This test indicates the presence of antibodies that prevent the influenza virus from attaching to red blood cells and is therefore indicative that the animal may have protective antibodies. The CDC and USDA-*APHIS*-Center for Veterinary Biologics report an 8-fold or greater reduction in HI titer a significant reduction in cross reactivity between virus hemagglutinin variants.

Thirty-eight serum samples from pigs vaccinated with 19 H1 SIV isolated from U.S commercial swine operations between 1999-2008 (NADC H1 serum reference panel) were tested in the standard HI test. The 19 H1 SIV in the NADC H1 serum reference panel used in this study represent all four phylogenetic (genetically characterized) clusters ($\alpha$, $\beta$, $\gamma$, and $\delta$) of all the endemic H1 swine influenza viruses known to circulate in the U.S. An additional 14 serum samples from pigs vaccinated with five different commercial products used to vaccinate pigs against H1 swine influenza viruses in the U.S were tested by the standard HI test.

Results:

Eleven of the thirty-eight serum samples from pigs inoculated with U.S HINT SW had a measurable HI titer against the A/CA/04/2009 H1N1 influenza virus. The same experiment with the A/NY/18/2009 H1N1 influenza virus had similar results. In contrast, twenty two of the thirty-eight serum samples from pigs inoculated with U.S H1 SIV had a measurable HI titer against the (A/Mexico/4108/2009) H1N1 influenza virus. Serologic cross-reactivity with antisera from 5 commercially-available SW H1 vaccines was additionally assessed by HI with the three 2009 A/H1N1 strains. Cross reactivity was consistently low between the vaccine antisera and all 2009 A/H1N1 novel strains tested, although titers were slightly higher with the isolate from Mexico. This suggests that currently available vaccines may provide only limited protection against challenge with the novel H1N1.

Conclusion:

Results of this experiment suggest that pre-existing immunity induced by swine influenza viruses circulating in the U.S swine herd may not protect pigs against the new 2009 A/H1N1 influenza viruses presently circulating in people. Importantly, vaccines currently used to protect pigs in U.S swine operations against swine influenza virus may not be effective against the new 2009 H1N1 influenza viruses.

Limited cross-reactivity of serum samples from the NADC H1 SIV antiserum reference panel or sera from pigs vaccinated with commercial vaccines was demonstrated against the 2009 A/H1N1 influenza virus (A/CA/04/2009) isolated in California as measured by a standard HI test. A second 2009 A/H1N1 strain from New York, A/NY/18/2009, was also used with the NADC H1 antiserum reference panel with very similar results to A/CA/04/2009. However, a third strain, A/Mexico/4108/2009, demonstrated broader cross-reactivity with the NADC H1 antiserum reference panel. This was especially apparent in the H1γ phylogenetic cluster. The cross-reactivity with the H1γ phylogenetic cluster is important since this is the genetic group in which the HA from the 2009 A/H1N1 originated. This would suggest that pre-existing immunity to certain currently circulating H1N1 SIV strains may protect against the outbreak virus. However, the differences between the novel H1N1 isolates suggest that there may be biologic variation in host and/or virus properties responsible for the variation in serologic crossreactivity.

It remains unknown whether this variation would have any effect on protection from live challenge in pigs from circulating strains of the 2009 A/H1N1 from the human population. Serologic cross-reactivity with anti-sera from 5 vaccines was also assessed by HI with the three 2009 A/H1N1 strains. Cross reactivity was consistently low between the vaccine antisera and all 2009 A/H1N1 novel strains, although titers were slightly higher with the isolate from Mexico. This suggests that currently available vaccines may provide only limited protection against challenge with the 2009 H1N1.

EXAMPLES

Proposed Experiments
Experiment 1—In Vitro Testing
Reactivity of A/H1N1 influenza A virus to uncoated pancreatic porcine enzyme dilutions in a pH neutral medium.

Purpose of Study

To address the efficacy of uncoated pancreatic porcine enzymes in eradicating or inhibiting the spread of various strains of A/H1N1 influenza virus by measuring the degradation in viral RNA integrity following exposure to an enzymatic preparation.

Experiment:

Influenza virus type A, H1N1, isolated from persons in various time periods and geographic locations will be obtained from the Centers for Disease Control and Prevention (CDC) or World Health Organization (WHO) and grown in vitro (i.e., in a permissive cell line). Appropriate viral containment facilities will be employed.

A/H1N1 virus will be grown in culture using infection into an appropriate cell host such as MDCK anchorage dependant cells cultures or CACO-2 cell lines. A/H1N1 viral particles shed into the culture medium will then be collected and the viral particle concentration determined using a real-time Reverse Transcriptase Polymerase Chain Reaction (rRT-PCR) based assay for a/H1N1 specific RNA. Porcine Enzyme Concentrate will then be added to a mixture of the viral particles prepared in standard cell culture growth media used with either of the above two named cell lines. Various dilutions will be prepared including 1:25, 1:50, 1:100, 1:200. Materials will be incubated for a period of time ranging from 30 minutes to 6 hours at 37 C. Virus particles will then be separated from the Enzyme preparation, reconstituted in growth medium and plated onto the CACO-2 or MDCK cell lines. Cells will be allowed to grow and titer of released viral particles over a period of 3 days will be determined. Controls will be prepared by exposing A/H1N1 viral particles to phosphate buffered saline solution at 37 C for identical times. Control particles will then be prepared and plated as per experimentally treated virus cultures.

Samples at 12 hour periods over the course of 3 days will be assayed using laboratory diagnostic testing for the presence of influenza viruses in the specimens. In addition to utilization of a Real-time Reverse Transcriptase Polymerase Chain Reaction based assay (rRT-PCR) that has been shown capable of detecting the A/H1N1 specific RNA, other tests may be used including direct antigen detection tests such as ELISA based assays for viral antigens and virus isolation in cell culture may be used.

Other rRT-PCR assays such as laboratory developed tests, not approved by FDA, may also be able to detect novel influenza A (H1N1) viruses. Public health laboratories in the U.S. are currently able to perform the CDC rRT-PCR Swine Flu Panel assay.

Anticipated Results:

Replication of A/H1N1 in a permissive cell line should be inhibited (static), reduced or eradicated (-cidal) by exposure to the pancreatic porcine enzyme dilutions as compared to control samples.

Experiment 2—In Vivo Testing

Effectiveness of coated pancreatic porcine enzyme on A/H1N1 influenza A virus symptoms or viral load in humans.

Purpose of Study

To address the efficacy of coated pancreatic porcine enzymes in eradicating or decreasing the symptoms or viral load of A/H1N1 influenza virus.

Experiment:

Candidate test subjects are those individuals who exhibit symptoms of A/H1N1 influenza A viruses and meet other test inclusion or exclusion criteria will be tested for presence of the virus using rapid A/H1N1 testing. Test Groups may be selected by age including infant and elderly, general health including healthy subjects and immuno-compromised subjects, geographic location, or other selection/exclusion criteria.

Rapid influenza diagnostic testing is utilized to identify candidate test subjects in a clinically relevant time period. Rapid influenza diagnostic tests (RIDTs) are typically antigen detection tests that detect influenza viral nucleoprotein antigen. The present commercially available test can provide results within 30 minutes or less. These assays may be referred to as "point-of care" tests since CLIA-waived RIDTs (not all RIDTs are CLIA waived) may be used in facilities with a certificate of waiver or in locations outside a central laboratory. Commercially available RTDTs can either: i) detect and distinguish between influenza A and B viruses; ii) detect both influenza A and B but not distinguish between influenza A and B viruses; or, iii) detect only influenza A viruses. None of the currently FDA approved RIDTs can distinguish between influenza A virus subtypes (e.g. seasonal influenza A (H3N2) versus seasonal influenza A (H1N1) viruses), and RTDTs cannot provide any information about antiviral drug susceptibility.

Once a positive result is obtained further swabs or test specimens are obtained from the test subjects for detailed laboratory analysis to validate positive test subject and isolate specific viral subtype(s). Laboratory tests may include direct antigen detection tests, virus isolation in cell culture, or detection of influenza-specific RNA by real-time reverse transcriptase-polymerase chain reaction (rRT-PCR).

Laboratory tests typically differ in their sensitivity and specificity in detecting influenza viruses as well as in their commercial availability, the amount of time needed from specimen collection until results are available, and the tests' ability to distinguish between different influenza virus types (A versus B) and influenza A subtypes (e.g. novel H1N1 versus seasonal H1N1 versus seasonal H3N2 viruses). At the present time, there are only two FDA authorized assays for confirmation of novel influenza A (H1N1) virus infection, including the CDC rRT-PCR Swine Flu Panel assay.

Other rRT-PCR assays such as laboratory developed tests, not approved by FDA, may also be able to detect novel influenza A (H1N1) viruses. Public health laboratories in the U.S. are currently able to perform the CDC rRT-PCR Swine Flu Panel assay Stool samples may be collected from the subjects both prior to the start of clinical testing and periodically during testing. This may especially important when testing immune-compromised individuals who may have low levels of chymotrypsin or other pancreatic secretions in their stool.

Coated Porcine Enzyme Concentrate will be administered to test subjects at appropriate doses with each major meal for a minimum of 3 dosings per day over a period of 7 to 10 days. Swabs or test specimens and, optionally, stool samples are collected on a daily basis for subsequent laboratory analysis over a clinically relevant time period such as 7 to 10 days. Patients will be observed for progression of symptoms, viral related sequelae and the presence of viral particles in collected samples over the course of treatment.

Placebos are also administered to a control sub group of test subjects at the same time intervals and swabs or test specimens and optionally stool samples are collected on a daily basis for subsequent laboratory analysis over a clinically relevant time period such as 7 to 10 days.

Anticipated Results:

Administration of coated pancreatic porcine enzymes to test subjects positive for A/H1N1 should decrease the severity and/or duration of associated symptoms. Additionally, compared to placebo treated patients, there should be an accelerated decrease in detectable virus obtained from physiological samples.

The foregoing description of the embodiments of the disclosure has been presented for the purposes of illustration and description. It is not intended to be exhaustive or to limit the disclosure to the precise form disclosed. Many modifications and variations are possible in light of this disclosure. It is intended that the scope of the disclosure be limited not by this detailed description, but rather by the claims appended hereto.

What is claimed is:

1. A method for the treatment of an Influenza virus in a mammal or a bird, comprising orally administering to the mammal or bird a therapeutically effective amount of a coated pharmaceutical composition containing a sole bioactive substance that consists of digestive enzymes; wherein the digestive enzymes comprise a combination of at least one lipase and at least one protease; and wherein the Influenza virus is treated.

2. The method of claim 1, wherein the Influenza virus comprises an Influenza Type A virus, an Influenza Type B virus, an Influenza Type C virus, a Subtype H1N1 virus, or a Subtype H5N1 virus.

3. The method of claim 1, wherein the digestive enzymes further comprise at least one amylase.

4. The method of claim 3, wherein the coated pharmaceutical composition comprises at least one amylase, at least one protease comprising chymotrypsin and trypsin, and at least one lipase.

5. The method of claim 3, wherein the digestive enzymes are provided as pancreatin.

6. The method of claim 3, wherein the at least one amylase is present in the coated pharmaceutical composition in an amount of from about 10,000 to about 60,000 U.S.P. units per dose.

7. The method of claim 1, wherein the digestive enzymes are pancreatic enzymes.

8. The method of claim 1, wherein the digestive enzymes comprise avian enzymes or pig enzymes.

9. The method of claim 1, wherein the at least one protease comprises chymotrypsin and trypsin.

10. The method of claim 9, wherein the chymotrypsin is present in the coated pharmaceutical composition in an amount of from about 2 to about 5 mg per dose, and wherein the trypsin is present in the coated pharmaceutical composition in an amount of from about 60 to about 100 mg per dose.

11. The method of claim 1, wherein the digestive enzymes are animal enzymes, microbial enzymes, plant enzymes, or are synthetic enzymes.

12. The method of claim 11, where the digestive enzymes are animal enzymes from a pig pancreas.

13. The method of claim 1, wherein the mammal is a pig, a horse, a cow, a dog, a cat, a monkey, a rat, a mouse, a sheep, a goat, or a human.

14. The method of claim 1, further comprising vaccinating the mammal or bird with a trivalent inactivated influenza vaccine (TIV) or a live, attenuated influenza vaccine (LAIV); treating the mammal or bird with an anti-viral medication; or both.

15. The method of claim 1, wherein the at least one protease and the at least one lipase in the pharmaceutical composition in United States Pharmacopoeia (U.S.P.) units are present in a ratio of protease to lipase of from about 1:1 to about 20:1.

16. The method of claim 1, wherein the at least one protease and the at least one lipase in the pharmaceutical composition in U.S.P. units are present in a ratio of protease to lipase of from about 4:1 to about 10:1.

17. The method of claim 1, wherein the coated pharmaceutical composition further comprises one or more enzymes selected from the group consisting of a cellulase, a sucrase, a maltase, and a hydrolase.

18. The method of claim 1, wherein the at least one protease is present in the coated pharmaceutical composition in an amount of from about 10,000 to about 70,000 U.S.P. units per dose.

19. The method of claim 1, wherein the at least one lipase is present in the coated pharmaceutical composition in an amount of from about 4,000 to about 30,000 U.S.P. units per dose.

20. The method of claim 1, wherein the at least one protease and the at least one lipase are present in the coated pharmaceutical composition in U.S.P. units in a ratio of protease to lipase of 4:1, 7:1, 10:1, or 12:1.

21. The method of claim 1, wherein the digestive enzymes are coated with a lipid or a lipid blend.

22. The method of claim 1, comprising administering at least two doses of the coated pharmaceutical composition to the mammal or bird.

23. The method of claim 1, comprising treating the mammal, wherein the mammal comprises a child under the age of 2.

24. A method for the treatment of an Influenza virus in a mammal having a subnormal level of fecal chymotrypsin (FCT), comprising orally administering to the mammal a therapeutically effective amount of a coated pharmaceutical composition containing a sole bioactive substance that consists of digestive enzymes; wherein the digestive enzymes comprise a combination of at least one lipase and at least one protease, and wherein the Influenza virus is treated.

25. The method of claim 24, wherein the digestive enzymes further comprise at least one amylase.

26. The method of claim 24, wherein the digestive enzymes are coated with a lipid or a lipid blend.

27. The method of claim 24, wherein the Influenza virus comprises an Influenza Type A virus, an Influenza Type B virus, an Influenza Type C virus, a Subtype H1N1 virus, or a Subtype H5N1 virus.

* * * * *